United States Patent
Kim et al.

(10) Patent No.: US 10,545,139 B2
(45) Date of Patent: Jan. 28, 2020

(54) METHODS AND DEVICES FOR PERFORMING BIOLOGICAL ASSAYS USING MAGNETIC COMPONENTS

(71) Applicant: Curiox Biosystems Pte Ltd., Singapore (SG)

(72) Inventors: Namyong Kim, Allston, MA (US); Hanwen Melvin Lye, Malden, MA (US); Kong Leong Cheng, Singapore (SG)

(73) Assignee: Curiox Biosystems Pte Ltd., Singapore (SG)

( * ) Notice: Subject to any disclaimer, the term of this patent is extended or adjusted under 35 U.S.C. 154(b) by 387 days.

(21) Appl. No.: 15/184,846

(22) Filed: Jun. 16, 2016

(65) Prior Publication Data
US 2017/0038372 A1    Feb. 9, 2017

Related U.S. Application Data

(60) Provisional application No. 62/180,259, filed on Jun. 16, 2015, provisional application No. 62/292,689, filed on Feb. 8, 2016.

(51) Int. Cl.
*G01N 33/543*    (2006.01)

(52) U.S. Cl.
CPC ............... *G01N 33/54326* (2013.01)

(58) Field of Classification Search
None
See application file for complete search history.

(56) References Cited

U.S. PATENT DOCUMENTS

| 3,426,108 A | 2/1969 | Britten |
| 3,754,872 A | 8/1973 | Zauft |
| (Continued) | | |

FOREIGN PATENT DOCUMENTS

| CN | 1460723 A | 12/2003 |
| CN | 1858593 A | 11/2006 |
| (Continued) | | |

OTHER PUBLICATIONS

Cheng, Final Office Action, U.S. Appl. No. 14/050,321, dated Jan. 24, 2018, 33 pgs.
(Continued)

*Primary Examiner* — Rebecca L Martinez
(74) *Attorney, Agent, or Firm* — Morgan, Lewis & Bockius LLP

(57) ABSTRACT

A method for retrieving magnetic components from a sample solution includes obtaining an array plate with a sample surface that includes a plurality of sample regions and a surrounding region. A first solution is located on a sample region of the plurality of sample regions. The first solution includes a plurality of magnetic components. A separation layer that includes one or more protrusions is placed so that at least a respective protrusion of the one or more protrusions is at least partially immersed in the first solution. A first magnetic device is placed within the respective protrusion. At least a portion of the plurality of magnetic components is retrieved from the first solution by concurrently moving the separation layer and the magnetic device so that the respective protrusion ceases to be at least partially immersed in the first solution on the sample region.

11 Claims, 33 Drawing Sheets

(56) References Cited

U.S. PATENT DOCUMENTS

| | | |
|---|---|---|
| 5,041,266 A | 8/1991 | Fox |
| 5,219,528 A | 6/1993 | Clark |
| 5,229,163 A | 7/1993 | Fox |
| 5,506,121 A | 4/1996 | Skerra et al. |
| 5,560,811 A | 10/1996 | Briggs et al. |
| 5,567,326 A * | 10/1996 | Ekenberg ............ B03C 1/0332 210/222 |
| 5,691,147 A | 11/1997 | Draetta et al. |
| RE35,894 E | 9/1998 | Ellison et al. |
| 5,817,510 A | 10/1998 | Pandey et al. |
| 6,048,908 A | 4/2000 | Kitagawa |
| 6,086,825 A | 7/2000 | Sundberg et al. |
| 6,103,493 A | 8/2000 | Skerra et al. |
| 6,121,055 A * | 9/2000 | Hargreaves ............ B01L 3/502 435/2 |
| 6,130,098 A | 10/2000 | Handique et al. |
| 6,238,626 B1 | 5/2001 | Higuchi et al. |
| 6,331,441 B1 | 12/2001 | Balch et al. |
| 6,534,014 B1 | 3/2003 | Mainquist et al. |
| 6,565,813 B1 | 5/2003 | Garyantes |
| 6,578,952 B1 | 6/2003 | Sugiyama et al. |
| 6,664,044 B1 | 12/2003 | Sato |
| 6,699,437 B1 | 3/2004 | Astle |
| 6,716,629 B2 | 4/2004 | Hess et al. |
| 6,767,733 B1 | 7/2004 | Green |
| 6,902,705 B1 | 6/2005 | Caillat et al. |
| 7,163,823 B2 | 1/2007 | Patno et al. |
| 7,439,056 B2 | 10/2007 | Duffy et al. |
| 7,344,877 B1 | 3/2008 | Camacho et al. |
| 7,666,362 B2 | 2/2010 | Shanler |
| 7,794,799 B1 | 9/2010 | Kim |
| 7,854,343 B2 | 12/2010 | Ellson et al. |
| 7,858,044 B2 | 12/2010 | Coassin et al. |
| 8,221,697 B2 | 7/2012 | Nichols et al. |
| 8,337,778 B2 | 12/2012 | Stone et al. |
| 8,987,174 B2 | 3/2015 | Routenberg |
| 2002/0016009 A1 | 2/2002 | Ogura |
| 2002/0064482 A1 | 5/2002 | Tisone et al. |
| 2002/0094533 A1 | 7/2002 | Hess |
| 2003/0032046 A1 | 2/2003 | Duffy et al. |
| 2003/0083474 A1 | 5/2003 | Schmidt |
| 2003/0113813 A1 | 6/2003 | Heidaran et al. |
| 2003/0124599 A1 | 7/2003 | Chen |
| 2003/0148401 A1 | 8/2003 | Agrawal et al. |
| 2003/0170613 A1 * | 9/2003 | Straus ............ G01N 33/56916 435/5 |
| 2003/0209560 A1 | 11/2003 | Hui et al. |
| 2004/0106156 A1 | 6/2004 | Perez |
| 2004/0106191 A1 | 6/2004 | Muser |
| 2004/0136876 A1 | 7/2004 | Fouillet et al. |
| 2004/0142460 A1 | 7/2004 | Cima |
| 2004/0208792 A1 | 10/2004 | Linton et al. |
| 2004/0234966 A1 | 11/2004 | Bryning |
| 2005/0045539 A1 | 3/2005 | Yu et al. |
| 2005/0079105 A1 | 4/2005 | Hunter et al. |
| 2005/0084423 A1 | 4/2005 | Zarowitz |
| 2005/0186579 A1 | 8/2005 | Dellinger |
| 2006/0013031 A1 | 1/2006 | Ravkin et al. |
| 2006/0051249 A1 | 3/2006 | Knebel et al. |
| 2006/0078893 A1 | 4/2006 | Griffiths |
| 2006/0105453 A1 | 5/2006 | Brenan et al. |
| 2006/0105462 A1 | 5/2006 | Sellek-Prince |
| 2006/0142468 A1 | 6/2006 | Downing, Jr. et al. |
| 2007/0003448 A1 | 1/2007 | Kanigan et al. |
| 2007/0005169 A1 | 1/2007 | Rohnert et al. |
| 2007/0077651 A1 | 4/2007 | Guarino |
| 2007/0099208 A1 | 5/2007 | Drmanac |
| 2007/0117765 A1 | 5/2007 | Sauve et al. |
| 2008/0003671 A1 | 1/2008 | Martin |
| 2008/0173544 A1 | 7/2008 | Seul |
| 2009/0142564 A1 | 6/2009 | Plissonnier et al. |
| 2009/0148348 A1 | 6/2009 | Pettigrew et al. |
| 2009/0227474 A1 | 9/2009 | Gordon et al. |
| 2009/0286317 A1 | 11/2009 | Demmler et al. |
| 2010/0000304 A1 | 1/2010 | Kim et al. |
| 2010/0167950 A1 | 7/2010 | Juang et al. |
| 2010/0297767 A1 | 11/2010 | Hattori et al. |
| 2012/0220497 A1 | 8/2012 | Jacobson et al. |
| 2015/0018248 A1 | 1/2015 | Kim |
| 2016/0169867 A1 | 6/2016 | Khine et al. |

FOREIGN PATENT DOCUMENTS

| | | |
|---|---|---|
| CN | 101031363 A | 9/2007 |
| DE | 10043042 C2 | 6/2002 |
| EP | 0812693 A1 | 12/1997 |
| EP | 1348533 B1 | 7/2002 |
| EP | 1358939 A2 | 4/2003 |
| EP | 1316360 B1 | 6/2003 |
| EP | 1386657 A1 | 2/2004 |
| EP | 1399263 B1 | 3/2004 |
| EP | 1473079 A1 | 11/2004 |
| EP | 1788047 A1 | 8/2005 |
| EP | 1683571 A1 | 1/2006 |
| GB | 1291610 | 10/1972 |
| GB | 2332273 A | 6/1999 |
| GB | 2334954 A | 9/1999 |
| JP | 3120453 B2 | 12/2000 |
| JP | 2002-502955 A | 1/2002 |
| JP | 2003-033177 A | 2/2003 |
| JP | 2004-020280 A | 1/2004 |
| JP | 2004-077476 A | 3/2004 |
| JP | 2004-535176 A | 11/2004 |
| JP | 2005-003803 A | 1/2005 |
| JP | 2005-099004 A | 4/2005 |
| WO | WO 1996-025879 | 8/1996 |
| WO | WO 1998-055852 | 12/1998 |
| WO | WO 99/39829 A1 | 8/1999 |
| WO | WO 2000-014311 | 3/2000 |
| WO | WO 00-58735 | 10/2000 |
| WO | WO 99/55826 | 10/2000 |
| WO | WO 2001-004144 A2 | 1/2001 |
| WO | WO 2003-029462 A1 | 4/2003 |
| WO | WO 2004-030820 A2 | 4/2004 |
| WO | WO 2004-111610 A2 | 12/2004 |
| WO | WO 2005/019254 A1 | 3/2005 |
| WO | WO 2005/019255 A1 | 3/2005 |
| WO | WO 2005/019256 A2 | 3/2005 |
| WO | WO 2006/004739 A2 | 1/2006 |
| WO | WO 2006/046699 A1 | 5/2006 |
| WO | WO 2007/102785 A1 | 9/2007 |
| WO | WO 2008/063136 A1 | 5/2008 |
| WO | WO 98/47003 | 10/2008 |
| WO | WO 2010/120249 A1 | 10/2010 |
| WO | WO 2012/011877 A2 | 1/2012 |

OTHER PUBLICATIONS

Kim, Notice of Allowance, U.S. Appl. No. 14/452,172, dated Dec. 12, 2017, 9 pgs.
Kim, Notice of Allowance, U.S. Appl. No. 14/338,168, dated Sep. 13, 2017, 8 pgs.
Leck, Office Action, U.S. Appl. No. 15/424,604, dated Aug. 11, 2017, 7 pgs.
Agency for Science, Technology and Research, Decision to Grant, Application No. CN201110401674.9, dated Aug. 7, 2014, 2 pages.
Agency for Science, Technology and Research, International Preliminary Report on Patentability, PCT/SG2007/000393, dated May 26, 2009, 4 pgs.
Agency for Science, Technology and Research, International Search Report and Written Opinion of the ISA, PCT/SG2007/000393, dated Feb. 20, 2008, 4 pgs.
Agency for Science, Technology and Research, Communication Pursuant to Article 94, EP07835548-4, dated Jul. 17, 2015, 3 pgs.
Agency for Science, Technology and Research, Notification of First Office Action, CN 201110401674.9, dated Dec. 30, 2013, 9 pgs.
Agency for Science, Technology and Research, First Examination Report, IN3674/CHEN/P2009, dated Oct. 7, 2016, 9 pgs.
Agency for Science, Technology and Research, Notification of Reasons for Refusal, JP 2009-538373, dated Nov. 11, 2011, 7 pgs.
Agency for Science, Technology and Research, Decision to Grant, JP2012-196318, dated Sep. 12, 2014, 3 pgs.

(56) References Cited

OTHER PUBLICATIONS

Agency for Science, Technology and Research, Notification of Reasons for Refusal, JP 2012-196318, dated Dec. 10, 2013, 3 pgs.
Agency for Science, Technology and Research, Notification of the First Office Action, CN 200780048922.8, dated Nov. 12, 2010, 4 pgs (available in Chinese only).
Agency for Science, Technology and Research, Notification of the Second Office Action, CN 200780048922.8, dated May 17, 2011, 4 pgs.
Agency for Science, Technology and Research, Notification on the Grant of Patent Right for Invention, CN 200780048922.8, dated Sep. 22, 2011, 1 pg.
Agency for Science, Technology and Research, Supplementary Search Report, EP 0783548.4, dated Jun. 30, 2010, 4 pgs.
Asberg, Surgace Energy Modified Chips for Detection of Conformational States and Enzymatic Activity in Biomolecules, Langmuir, 2006, pp. 2205-2211.
Beck, Improving Stamps for 10 nm Level Wafer Scale Nanoimprint Lithography, Microelectron. Eng., 2002, pp. 61-62 and 441.
Benor, Microstructuring by Microcontact Printing and Selective Surface Dewetting, J. of Vacuum Science & Technology B, 2007, pp. 1321-1326.
Beste, Small Antibody-like Proteins with Prescrived Ligand Specificities Derived from the Lipocalin Fold, Proc. Natl. Acad. Sci, USA, 1999, pp. 1898-1903.
Biffinger, The Polar Hydrophobicity of Chluorinated Compounds, ChemBioChem, 2004, pp. 622-627.
Burbulis, Quantifying Small Numbers of Antibodies with a 'Near-Universal' Protein-DNA Chimera, Nature Methods, Nov. 2007, 39 pgs.
Cheng, Office Action, U.S. Appl. No. 14/050,321, dated Feb. 26, 2016, 31 pgs.
Cheng, Office Action, U.S. Appl. No. 14/050,321, dated Mar. 31, 2017, 38 pgs.
Chiriac, Magnetic GMI Sensor for Detection of Biomolecules, J. Magnetism and Magnetic Materials, 2005, pp. 671-676.
Churaev, Wetting of Low-Energy Surgfaces, Advances in Colloid and Interface Science, 2007, pp. 134-135, 15-23.
Curiox Biosystems Pte Ltd, International Preliminary Report on Patentability, PCT/SG2010/000153, dated Oct. 18, 2011, 15 pgs.
Curiox Biosystems Pte Ltd, International Preliminary Report on Patentability, PCT/SG2011/000263, dated Dec. 21, 2012, 5 pgs.
Curiox Biosystems Pte Ltd, International Search Report and Written Opinion, PCT/IB2013/000623, dated Jul. 10, 2013, 10 pgs.
Curiox Biosystems Pte Ltd, International Preliminary Report on Patentablity, PCT/IB2013/000623, dated Aug. 5, 2014, 7 pgs.
Curiox Biosystems Pte Ltd, International Search Report and Written Opinion, PCT/SG2006/000050, dated May 8, 2006, 6 pgs.
Curiox Biosystems Pte Ltd, International Search Report and Written Opinion, PCT/SG2010/000153, dated Sep. 17, 2010, 20 pgs.
Curiox Biosystems Pte Ltd, International Search Report and Written Opinion, PCT/SG2011/000263, dated Feb. 29, 2012, 18 pgs.
Curiox Biosystems Pte Ltd, International Search Report and Written Opinion, PCT/US2015/019760, dated Jun. 2, 2015, 12 pgs.
Daniel, Vibration-Actuated Drop Motion on Surfaces bor Batch Microfluidic Processes, Langmuir, 2005, pp. 4220-4228.
Dill, Modeling Water, The Hydrophobic Effect and Ion Solvation, Annu. Rev. Biophys. Biomol. Struc, 2005, pp. 173-199.
Erfle et al., "Reverse Transfections on Cell Arrays for High Content Screening Microscopy," Nature Protocols, Mar. 1, 2007, vol. 2 No. 2, 8 pgs.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp. 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.

Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodies: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem, Eng. Aspects, 2006, pp. 33-40.
Jung, Wetting Transition of Water Droplets on Superhydrophobic Patterned Surfaces, Scripta Materialia, 2007, pp. 1057-1060.
Kanta, Preparation of Silica-on-Titania Patterns with a Wettability Contrast, Langmuir, 2005, 5790-5794.
Kim, Final Office Action, U.S. Appl. No. 13/264,913, dated Jun. 21, 2013, 11 pgs.
Kim, Notice of Allowance, U.S. Appl. No. 12/282,162, dated May 14, 2012, 7 pgs.
Kim, Office Action, U.S. Appl. No. 12/282,162, dated Jun. 27, 2011, 8 pgs.
Kim, Office Action, U.S. Appl. No. 13/264,913, dated Nov. 7, 2012, 9 pgs.
Kim, Office Action, U.S. Appl. No. 13/264,913, dated Sep. 26, 2013, 10 pgs.
Kim, Office Action, U.S. Appl. No. 13/811,638, dated Sep. 11, 2015, 29 pgs.
Kim, Final Office Action, U.S. Appl. No. 13/811,638, dated Apr. 21, 2016, 24 pgs.
Kim, Final Office Action, U.S. Appl. No. 13/811,638, dated Feb. 9, 2017, 29 pgs.
Kim, Office Action, U.S. Appl. No. 14/326,780, dated Oct. 28, 2015, 13 pgs.
Kim, Final Office Action, U.S. Appl. No. 14/326,780, dated May 10, 2016, 11 pgs.
Kim, Notice of Allowance, U.S. Appl. No. 14/326,780, dated Sep. 26, 2016, 7 pgs.
Kim, Office Action, U.S. Appl. No. 14/452,172, dated Oct. 23, 2015, 16 pgs.
Kim, Final Office Action, U.S. Appl. No. 14/452,172, dated Jun. 3, 2016, 17 pgs.
Kim, Office Action, U.S. Appl. No. 14/338,168, dated Nov. 6, 2015, 8 pgs.
Kim, Office Action, U.S. Appl. No. 14/338,168, dated Jun. 22, 2016, 9 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. AM. Chem. Soc., 2007, pp. 1508-1509.
Leek, Final Office Action, U.S. Appl. No. 11/984,197, dated May 8, 2012, 10 pgs.
Leek, Office Action, U.S. Appl. No. 11/984,197, dated Mar. 14, 2013, 11 pgs.
Leek, Office Action, U.S. Appl. No. 11/984,197, dated May 26, 2011, 11 pgs.
Leek, Office Action, U.S. Appl. No. 11/984,197, dated Jul. 31, 2013, 12 pgs.
Leek, Notice of Allowance, U.S. Appl. No. 14/246,004, dated Sep. 15, 2016, 8 pgs.
Li, What Do We Need for a Superhydrophobic surface? A review on the recent progress in the preparation of superhydrophobic surfaces, Chem. Soc. Rev, 2007, pp. 1350-1368.
Lowe et al., "Perfluorochemicals: Their Applications and Benefits to Cell Culture," Tibtech, Jun. 1998, vol. 16, 6 pgs.

(56) References Cited

OTHER PUBLICATIONS

Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.
Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp. 4517-4527.
Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Perfulorodecalin-FluoroMed, downloaded on Sep. 5, 2013, from http://fluoromed.com/products/perfluorodecalin.html, 1 pg.
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludies, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.
Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of *Sscherichi coli* O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophobic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Takahashi et al., Induction of Pluripotent Stem Cells from Mouse Embryonic and Adult Fibroblast Cultures by Defined Factors, Cell, Aug. 25, 2006, 126, 14 pgs.
Vancha et al., "Use of Polyethyleneimine Polymer in Cell Culture as Attachment Factor and Lipofection Enhancer," BMC Biotechnology, Oct. 15, 2004, 12 pgs.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfluidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.
Washizu, Elecrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem. Phys., 2003, pp. 3085-3093.
Wixforth, Flatland Fluidics, mstnews, 2002, pp. 42-43.

\* cited by examiner

500

502 Obtain an array plate with a sample surface that includes a plurality of sample regions and a surrounding region. The plurality of sample regions has a first surface tension. The surrounding region has a second surface tension that is distinct from the first surface tension. A sample solution is located on a sample region of the plurality of sample regions. The sample solution includes a plurality of target molecules. The sample solution includes a plurality of magnetic beads, respective magnetic beads of the plurality of magnetic beads configured to couple with respective target molecules.

504 The respective magnetic beads have respective signatures

506 Incubate the sample solution while one or more magnetic devices are positioned adjacent to the sample solution

508 Agitate the sample solution while incubating the sample solution

509 Incubate the sample solution without agitating the sample solution

510 Wash the plurality of magnetic beads to obtain target molecules bound to at least a subset of the plurality of magnetic beads

512 Detect the target molecules bound to at least the subset of the plurality of magnetic beads

514 Add to the sample solution a plurality of detection molecules configured to couple with the respective target molecules

516 Wash the plurality of magnetic beads to obtain target molecules bound to at least a subset of the plurality of magnetic beads and at least a subset of the plurality of detection molecules

518 Detect a combination of a respective target molecule coupled with a respective magnetic bead and a respective detection molecule

702 Obtain an array plate with a sample surface that includes a plurality of sample regions and a surrounding region. The plurality of sample regions has a first surface tension. The surrounding region has a second surface tension that is distinct from the first surface tension. A first sample region of the plurality of sample regions has a first set of magnetic beads each configured to couple with a target molecule of a first type. A second sample region of the plurality of sample regions has a second set of magnetic beads each configured to couple with a target molecule of a second type that is distinct from a target molecule of the first type.

704 The first sample region of the plurality of sample regions has a third set of magnetic beads each configured to couple with a target molecule of a third type that is distinct from a target molecule of the first type and a target molecule of the second type. The second sample region of the plurality of sample regions has a fourth set of magnetic beads each configured to couple with a target molecule of a fourth type that is distinct from a target molecule of the first type, a target molecule of the second type, and a target molecule of the third type.

706 The first set of magnetic beads is associated with a first signal. The second set of magnetic beads is associated with a second signal that is distinct from the first signal. The third set of magnetic beads is associated with a third signal. The fourth set of magnetic beads is associated with a fourth signal that is distinct from the third signal.

708 The third signal is identical to either the first signal or the second signal

↓

710 Position one or more magnetic devices adjacent to the first sample region and the second sample region to retain the magnetic beads on the first sample region and the second sample region

↓

712 Provide a sample solution over multiple sample regions, including the first sample region and the second sample region, of the plurality of sample regions so that a single contiguous volume of the sample solution is in contact with the multiple sample regions, including the first sample region and the second sample region, while the magnetic beads on the first sample region and the second sample region are retained by the one or more magnetic devices

↓

714 Incubate the sample solution while one or more magnetic devices are positioned adjacent to the first sample region and the second sample region

↓

716 Wash the magnetic beads to obtain target molecules bound to at least a subset of the magnetic beads on the first and/or second sample region(s)

902 Obtain an array plate with a sample surface that includes a plurality of sample regions and a surrounding region. A first solution is located on a sample region of the plurality of sample regions. The first solution includes a plurality of magnetic components.

> 904 The first solution includes a plurality of target molecules; and respective magnetic components of the plurality of magnetic components are configured to couple with respective target molecules.

> 906 The plurality of sample regions has a first surface tension; and the surrounding region has a second surface tension that is distinct from the first surface tension.

908 Place the separation layer and the first magnetic device adjacent to the second solution so that the retrieved portion of the plurality of magnetic components and at least a portion of the respective protrusion are immersed in the second solution > 910 Prior to placing the separation layer: incubate the first solution; and wash the plurality of magnetic components to obtain target molecules bound to at least a subset of the plurality of magnetic components
>
> > 912 Incubate the first solution while one or more magnetic devices are positioned adjacent to the first solution, underneath the first solution
>
> > 914 Wash the plurality of magnetic components while one or more magnetic devices are positioned adjacent to the first solution, underneath the first solution

916 Place a first magnetic device within the respective protrusion (A)

Figure 9A

918 Retrieve at least a portion of the plurality of magnetic components from the first solution by separating the separation layer and the magnetic device from the first solution so that the respective protrusion ceases to be at least partially immersed in the first solution on the sample region 920 Obtain a second array plate with a second sample surface that includes a second plurality of sample regions and a second surrounding region. A second solution is located on a sample region of the second plurality of sample regions. Place the separation layer and the first magnetic device adjacent to the second solution so that the retrieved portion of the plurality of magnetic components and at least a portion of the respective protrusion are immersed in the second solution. While a second magnetic device is placed adjacent to the second solution, move the first magnetic device away from the separation layer. Subsequent to moving the first magnetic device away from the separation layer, move the separation layer so that the portion of the respective protrusion that was previously immersed in the second solution ceases to be immersed in the second solution.

922 Position the second magnetic device to move the retrieved portion of the plurality of magnetic components to a first location within the second solution. Aspirate at least a portion of the second solution from a location within the second solution that is distinct from the first location.

924 Position a third magnetic device, that is distinct from the second magnetic device, to move the retrieved portion of the plurality of magnetic components to a first location within the second solution. Aspirate at least a portion of the second solution from a location within the second solution that is distinct from the first location.

926 Prior to positioning the magnetic device, agitate the second solution

928 Analyze the aspirated solution

Figure 9B

METHODS AND DEVICES FOR PERFORMING BIOLOGICAL ASSAYS USING MAGNETIC COMPONENTS

RELATED APPLICATIONS

This application claims the benefit of, and priority to, U.S. Provisional Patent Application Ser. No. 62/180,259, filed Jun. 16, 2015, entitled "Methods and Devices for Performing Biological Assays Using Magnetic Components" and U.S. Provisional Patent Application Ser. No. 62/292,689, filed Feb. 8, 2016, entitled "Methods and Devices for Retrieving Magnetic Components from Sample Solution," both of which are incorporated by reference herein in their entireties.

This application is related to the following applications: (1) U.S. patent application Ser. No. 11/984,197, filed Nov. 14, 2007, which is a continuation-in-part of Patent Cooperation Treaty Application Serial No. PCT/SG2006/000363, filed Nov. 24, 2006; (2) U.S. patent application Ser. No. 12/282,162, filed Jan. 22, 2009, which is a national phase application of Patent Cooperation Treaty Application Serial No. PCT/SG06/00050, filed Mar. 9, 2006; (3) U.S. patent application Ser. No. 13/264,913, filed Oct. 17, 2011, which is a national phase application of Patent Cooperation Treaty Application Serial No. PCT/SG2010/000153, filed Apr. 16, 2010, which claims priority to U.S. Provisional Patent Application Ser. No. 61/170,201, filed Apr. 17, 2009; (4) U.S. patent application Ser. No. 13/811,638, filed Jan. 22, 2013, which is a national phase application of Patent Cooperation Treaty Application Serial No. PCT/SG2011/000263, filed Jul. 25, 2011, which claims priority to U.S. Provisional Patent Application Ser. No. 61/367,049, filed Jul. 23, 2010; (5) U.S. Provisional Application Ser. No. 61/711,725, filed Oct. 9, 2012; (6) Patent Cooperation Treaty Application Serial No. PCT/US2013/024783, filed Feb. 5, 2013, which claims priority to U.S. Provisional Patent Application Ser. No. 61/595,131, filed Feb. 5, 2012 and U.S. Provisional Patent Application Ser. No. 61/711,127, filed Oct. 8, 2012; and (7) U.S. patent application Ser. No. 14/338,168, filed Jul. 22, 2014, which is (i) a continuation-in-part of U.S. patent application Ser. No. 13/264,913, filed Oct. 17, 2011, which is a national stage application of International Application Serial No. PCT/SG2010/000153, filed Apr. 16, 2010, which claims priority to U.S. Provisional Patent Application Ser. No. 61/170,201, filed Apr. 17, 2009, and (ii) a continuation-in-part of U.S. patent application Ser. No. 14/246,004, filed Apr. 4, 2014, which is a continuation application of U.S. patent application Ser. No. 11/984,197, filed Nov. 14, 2007, which is a continuation-in-part of International Application Serial No. PCT/SG2006/000363, filed Nov. 24, 2006. This application is also related to U.S. Provisional Patent Application Ser. No. 62/180,259, filed Jun. 16, 2015. All of these applications are incorporated by reference herein in their entirety.

TECHNICAL FIELD

This application generally relates to methods and devices for handling small volumes of liquids and, more particularly, methods and devices for performing biological assays using magnetic particles.

BACKGROUND

Biological assays using magnetic components (e.g., magnetic particles, magnetic components, etc.) are gaining popularity. However, there are several limitations associated with the use of magnetic components in conventional well plates for biological assays.

SUMMARY

Accordingly, there is a need for methods and devices for more effectively performing biological assays with magnetic components. Such methods and devices may replace the conventional methods and devices for performing biological assays with magnetic components. Such methods and devices may complement the conventional methods and devices for performing biological assays with magnetic components.

In accordance with some embodiments, a method includes obtaining an array plate with a sample surface that includes a plurality of sample regions and a surrounding region. The plurality of sample regions has a first surface tension. The surrounding region has a second surface tension. In some embodiments, the second surface tension is distinct from the first surface tension. A sample solution is located on a sample region of the plurality of sample regions. The sample solution includes a plurality of target molecules. The sample solution includes a plurality of magnetic components, respective magnetic components of the plurality of magnetic components configured to couple with respective target molecules. The method also includes incubating the sample solution while one or more magnetic devices are positioned adjacent to the sample solution; and washing the plurality of magnetic components to obtain target molecules bound to at least a subset of the plurality of magnetic components.

In accordance with some embodiments, a method includes obtaining an array plate with a sample surface that includes a plurality of sample regions and a surrounding region. The plurality of sample regions has a first surface tension. The surrounding region has a second surface tension. In some embodiments, the second surface tension is distinct from the first surface tension. A sample solution is located on a sample region of the plurality of sample regions. The sample solution includes a plurality of magnetic components configured to couple with respective target molecules. The sample solution includes a plurality of target molecules, at least a subset of the target molecules coupled with respective detection molecules and separated from the plurality of magnetic components. The method also includes positioning one or more magnetic devices adjacent to the sample solution; subsequent to positioning one or more magnetic devices adjacent to the sample solution, moving the one or more magnetic devices and/or the array plate so that the plurality of magnetic components are spatially separated from at least the subset of the target molecules coupled with the respective detection molecules; and detecting the respective detection molecules in the sample solution.

In accordance with some embodiments, a method includes obtaining an array plate with a sample surface that includes a plurality of sample regions and a surrounding region. The plurality of sample regions has a first surface tension. The surrounding region has a second surface tension. In some embodiments, the second surface tension is distinct from the first surface tension. A first sample region of the plurality of sample regions has a first set of magnetic components each configured to couple with a target molecule of a first type. A second sample region of the plurality of sample regions has a second set of magnetic components each configured to couple with a target molecule of a second type that is distinct from a target molecule of the first type. The method also includes positioning one or more magnetic devices adjacent to the first sample region and the second sample region to retain the magnetic components on the first sample region and the second sample region; and providing a sample solution over multiple sample regions, including the first sample region and the second sample region, of the plurality of sample regions so that a single contiguous volume of the sample solution is in contact with the multiple sample regions, including the first sample region and the second sample region, while the magnetic components on the first sample region and the second sample region are retained by the one or more magnetic devices. The method further includes incubating the sample solution while one or more magnetic devices are positioned adjacent to the first sample region and the second sample region, and washing the magnetic components to obtain target molecules bound to at least a subset of the magnetic components on the first sample region and/or the second sample region.

In accordance with some embodiments, a system includes an array plate with a sample surface that includes a plurality of sample regions and a surrounding region. The plurality of sample regions has a first surface tension. The surrounding region has a second surface tension. In some embodiments, the second surface tension is distinct from the first surface tension. The system also includes a plurality of magnetic devices positioned adjacent to the array plate. A respective magnetic device is aligned with a respective sample region.

In accordance with some embodiments, a system includes an array plate with a sample surface that includes a plurality of sample regions and a surrounding region. The plurality of sample regions has a first surface tension. The surrounding region has a second surface tension. In some embodiments, the second surface tension is distinct from the first surface tension. A first sample region of the plurality of sample regions is configured to couple with a target molecule of a first type. A second sample region of the plurality of sample regions is configured to couple with a target molecule of a second type.

In accordance with some embodiments, a system includes an array plate with a sample surface that includes a plurality of sample regions and a surrounding region. The plurality of sample regions has a first surface tension. The surrounding region has a second surface tension. In some embodiments, the second surface tension is distinct from the first surface tension. A first sample region of the plurality of sample regions has a first set of magnetic components each configured to couple with a target molecule of a first type. A second sample region of the plurality of sample regions has a second set of magnetic components each configured to couple with a target molecule of a second type that is distinct from a target molecule of the first type.

In some embodiments, the first sample region of the plurality of sample regions has a third set of magnetic components each configured to couple with a target molecule of a third type that is distinct from a target molecule of the first type and a target molecule of the second type; and the second sample region of the plurality of sample regions has a fourth set of magnetic components each configured to couple with a target molecule of a fourth type that is distinct from a target molecule of the first type, a target molecule of the second type, and a target molecule of the third type.

In some embodiments, the first set of magnetic components is associated with a first signal; the second set of magnetic components is associated with a second signal that is distinct from the first signal; the third set of magnetic components is associated with a third signal; and the fourth set of magnetic components is associated with a fourth signal that is distinct from the third signal.

In some embodiments, the third signal is identical to either the first signal or the second signal.

In some embodiments, the plurality of sample regions includes a first set of sample regions and a second set of sample regions that is adjacent to the first set of sample regions; and the first set of sample regions is separated from the second set of sample regions by a distance that is longer than a distance between two adjacent sample regions within the first set.

In accordance with some embodiments, a method includes obtaining an array plate with a sample surface that includes a plurality of sample regions and a surrounding region. A first solution is located on a sample region of the plurality of sample regions. The first solution includes a plurality of magnetic components. The method also includes placing a separation layer that includes one or more protrusions so that at least a respective protrusion of the one or more protrusions is at least partially immersed in the first solution, placing a first magnetic device within the respective protrusion, and retrieving at least a portion of the plurality of magnetic components from the first solution by concurrently moving the separation layer and the magnetic device so that the respective protrusion ceases to be at least partially immersed in the first solution on the sample region.

Thus, described methods and systems provide improved efficiency and accuracy in performing biological assays with magnetic components. Such methods and systems may complement or replace conventional methods and systems for performing biological assays with magnetic components.

BRIEF DESCRIPTION OF THE DRAWINGS

For a better understanding of the aforementioned embodiments as well as additional embodiments, reference should be made to the Description of Embodiments below, in conjunction with the following drawings in which like reference numerals refer to corresponding parts throughout the figures.

FIG. 5 is a flow diagram illustrating a method of obtaining target molecules bound to magnetic components in accordance with some embodiments.

FIG. 7 is a flow diagram illustrating a method of obtaining target molecules bound to magnetic components in accordance with some embodiments.

FIGS. 9A-9B are flow diagrams illustrating a method of retrieving magnetic components from a solution in accordance with some embodiments.

Like reference numerals refer to corresponding parts throughout the drawings. Drawings are not drawn to scale unless explicitly stated otherwise.

DETAILED DESCRIPTION

Methods and devices described herein allow for more efficient and accurate biological assays. By using magnetic components (e.g., magnetic beads, magnetic particles, etc.) in an array plate that has regions of different hydrophobicities, limitations in performing biological assays with magnetic components in conventional well plates can be overcome. Details of several embodiments are discussed below.

Reference will be made to certain embodiments, examples of which are illustrated in the accompanying drawings. While the claims will be described in conjunction with the embodiments, it will be understood that it is not intended to limit the claims to these particular embodiments alone. On the contrary, the embodiments are intended to cover alternatives, modifications and equivalents that are within the spirit and scope of the appended claims.

Moreover, in the following description, numerous specific details are set forth to provide a thorough understanding of the embodiments. However, it will be apparent to one of ordinary skill in the art that the embodiments may be practiced without these particular details. In other instances, methods, procedures, components, and networks that are well-known to those of ordinary skill in the art are not described in detail to avoid obscuring aspects of the embodiments.

The terminology used in the description of the embodiments herein is for the purpose of describing particular embodiments only and is not intended to be limiting of the invention. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1A:
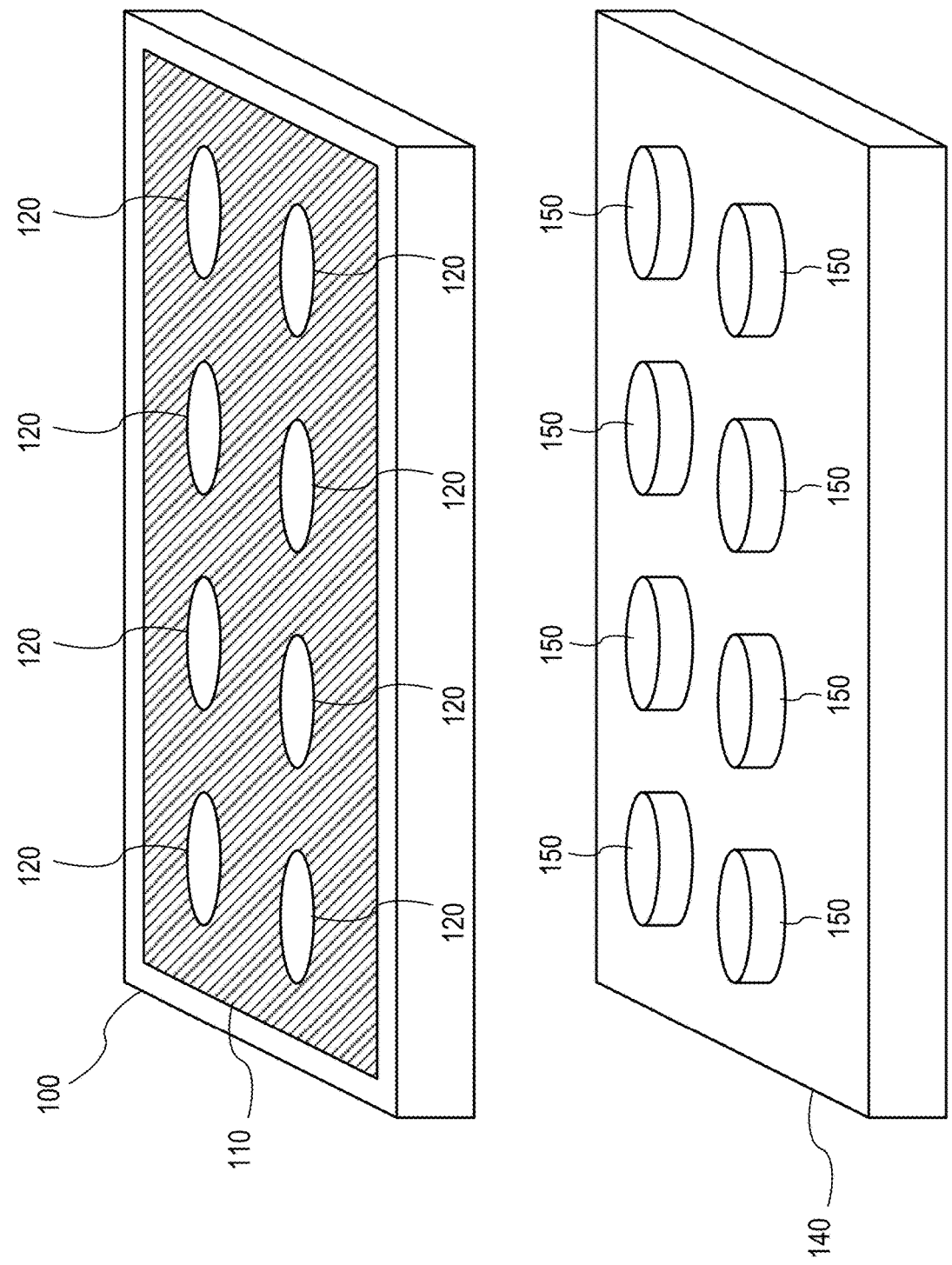
FIGS. 1A-1B are perspective views of an array plate and a magnetic device plate in accordance with some embodiments.
Figure 1B:
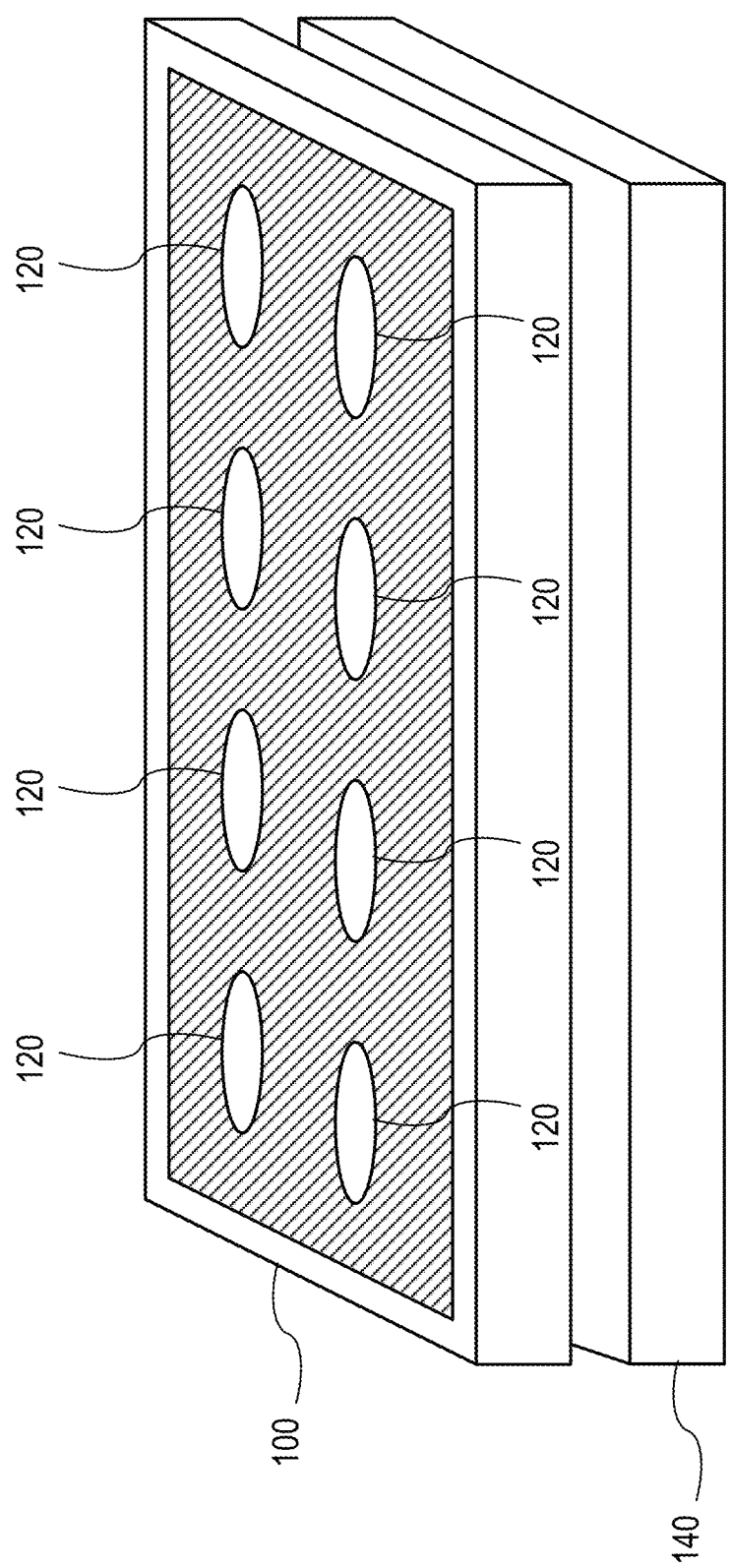

FIGS. 1A-1B are perspective views of exemplary array plate 100 and magnetic device plate 140 in accordance with some embodiments.

Exemplary array plate 100 includes an array of sample regions 120. In some embodiments, sample regions 120 are surrounded by one or more surrounding regions 110. In some embodiments, sample regions 120 are hydrophilic regions. In some embodiments, surrounding region 110 is a hydrophobic region. In some embodiments, sample regions 120 are hydrophobic regions and surrounding region 110 is a hydrophilic region. In some embodiments, the hydrophilic and hydrophobic regions are formed by using different materials (e.g., hydrophilic material for the hydrophilic regions and hydrophobic material for hydrophobic regions). In some embodiments, the hydrophilic and hydrophobic regions are formed by chemically or physically treating a surface of array plate 100.

In some embodiments, as illustrated in FIG. 1A, array plate 100 has a flat continuous surface. For example, sample regions 120 and surrounding region 110 are formed on the flat continuous surface. In some other embodiments, sample regions 120 and the one or more surrounding regions 110 are formed on different surfaces (e.g., sample regions 120 protrude from surrounding region 110 or are indented).

In FIG. 1A, magnetic device plate 140 includes a plurality of magnetic devices 150 (e.g., magnets). In some embodiments, magnetic devices 150 include permanent magnets. In some embodiments, magnetic devices 150 include electromagnets (e.g., an electric coil coupled with a current source, capable of generating a magnetic field). In some embodiments, magnetic devices 150 in magnetic device plate 140 are aligned with sample regions 120 in array plate 100. In some embodiments, magnetic device plate 140 includes fewer magnetic devices 150 than a number of sample regions 120 in array plate 100. In some embodiments, magnetic device plate 140 includes one magnetic device 150.

FIG. 1A illustrates that magnetic device plate 140 is positioned at a distance from array plate 100 so that the magnetic field applied by magnetic devices 150 on array plate 100 is reduced (e.g., at least some of the magnetic particles on array plate 100 are not held down by the magnetic force applied by magnetic devices 150).

In comparison, FIG. 1B illustrates that magnetic device plate 140 is positioned adjacent to array plate 100 so that the magnetic field applied by magnetic devices 150 on sample regions 120 is increased (e.g., at least some of the magnetic particles on array plate 100 are held down by the magnetic force applied by magnetic devices 150, pulling the magnetic particles toward magnetic devices 150).

Alternatively, when magnetic device plate 140 includes electromagnets, the magnetic field applied by magnetic devices 150 on sample regions 120 is turned on or off by controlling an electrical current provided to the electromagnets.

FIGS. 2A-2G are partial cross-sectional views of a system in accordance with some embodiments.

Figure 2A:
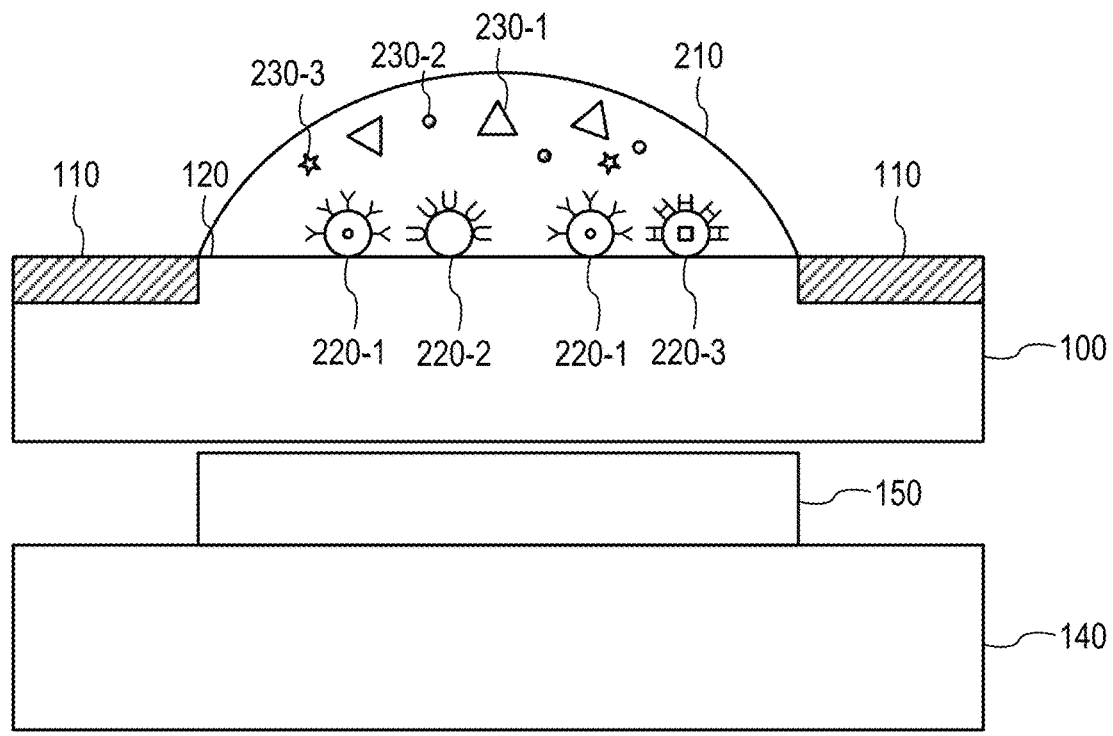
FIGS. 2A-2G are partial cross-sectional views of a system in accordance with some embodiments.

FIG. 2A illustrates that sample solution 210 is located on sample region 120. Sample solution 210 includes a plurality of magnetic components (e.g., magnetic beads, magnetic particles, etc.) 220-1, 220-2, and 220-3. Respective magnetic components 220 are configured to couple with respective target molecules 230 (e.g., proteins, nucleic acids, peptides, etc.). For example, magnetic components 220 are coated with antibodies configured to bind with antigens, or with oligonucleotides configured to capture target nucleic acid molecules. In some embodiments, magnetic component 220 is coated with particular antibodies (e.g., capture antibodies) that are configured to capture particular target molecules 230. In FIG. 2A, magnetic component 220-1 is coated with antibodies that are configured to capture target molecule 230-1, and magnetic component 220-2 is coated with antibodies that are configured to capture target molecules 230-2. Due to the positioning of magnetic device 150 adjacent to sample region 120, magnetic components 220 are located close to the surface of sample region 120 (e.g., magnetic components 220 are pulled toward the surface of sample region 120).

In some embodiments, magnetic components 220 are associated with respective signals (e.g., optical signals). For example, when illuminated with a light source (e.g., light from a light-emitting diode or a laser), magnetic component 220-1 emits light of a first wavelength pattern, magnetic component 220-2 emits light of a second wavelength pattern that is distinct from the first wavelength pattern, and magnetic component 220-3 emits light of a third wavelength pattern that is distinct from the first wavelength pattern and the second wavelength pattern. Thus, based on the wavelength pattern of the light emitted by respective magnetic component, an identity of the respective magnetic component can be determined (e.g., whether the respective magnetic component is magnetic component 220-1, magnetic component 220-2, or magnetic component 220-3 can be determined). In some embodiments, magnetic component 220 is embedded with material that emits light of a particular wavelength pattern when illuminated with a light source. In some embodiments, magnetic component 220 is coated with material that emits light of a particular wavelength pattern when illuminated with a light source.

FIG. 2A also illustrates that sample solution 210 includes a plurality of target molecules 230-1, 230-2, and 230-3. Target molecules 230 include analytes whose presence and quantity in sample solution 210 are to be determined.

Figure 2B:
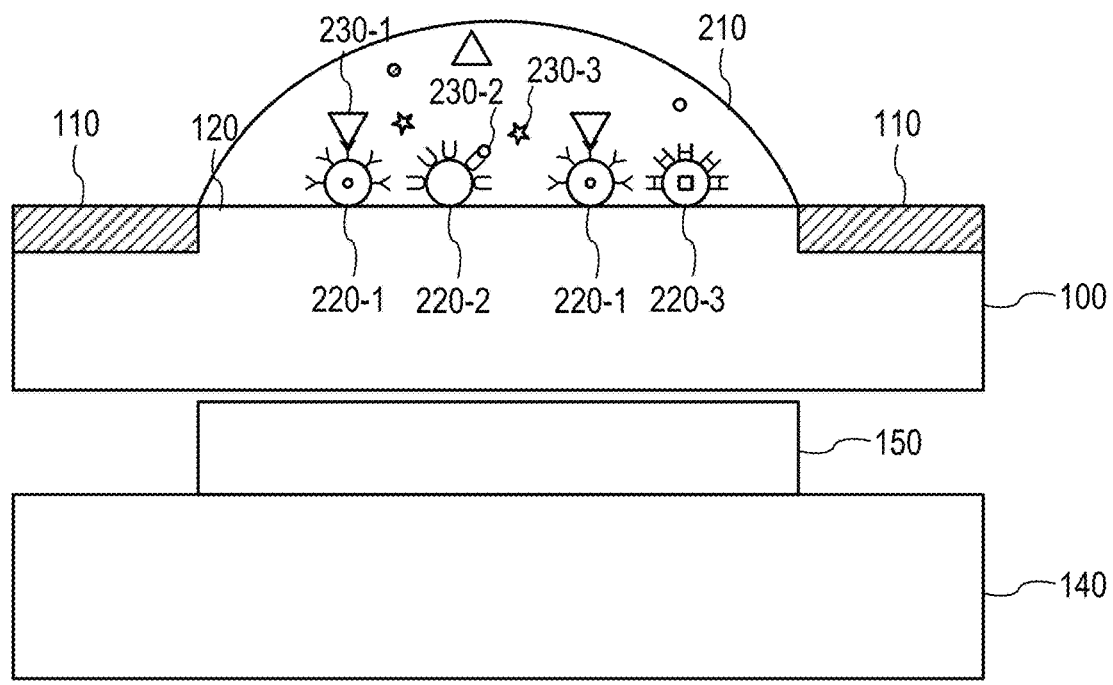

By incubating sample solution 210 (e.g., waiting for 2-24 hours), at least some of target molecules 230 bind to magnetic components 220 (or antibodies coating magnetic components 220), as shown in FIG. 2B. In some embodiments, sample solution 210 is agitated (e.g., by agitating or shaking array plate 100) during the incubation. Agitating sample solution 219 increases the movement of target molecules 230, which facilitates binding of target molecules 230 with antibodies on magnetic components 220.

Conventionally, it has been believed that magnetic components 220 should freely float during incubation (e.g., in the absence of any adjacent magnet) to improve binding of target molecules 230 to magnetic components 220. However, the inventor of this application has made a surprising discovery that placing magnetic device 150 adjacent to sample region 120, which pulls magnetic components 220 toward a surface of array plate 100, does not adversely affect binding of target molecules 230 to magnetic components 220. Furthermore, the inventor of this application has made a surprising discovery that placing magnetic device 150 adjacent to sample region 120 reduces challenges associated with incubation in the absence of any adjacent magnet, as described below with respect to FIGS. 2I-2J.

FIG. 2B also illustrates that sample solution 210 includes target molecules 230 that are not bound to magnetic components 220 (e.g., due to the absence of magnetic components coated with corresponding capture antibodies, the excess amount of target molecules 230, the affinity between the antibodies and target molecules 230, etc.).

Figure 2C:
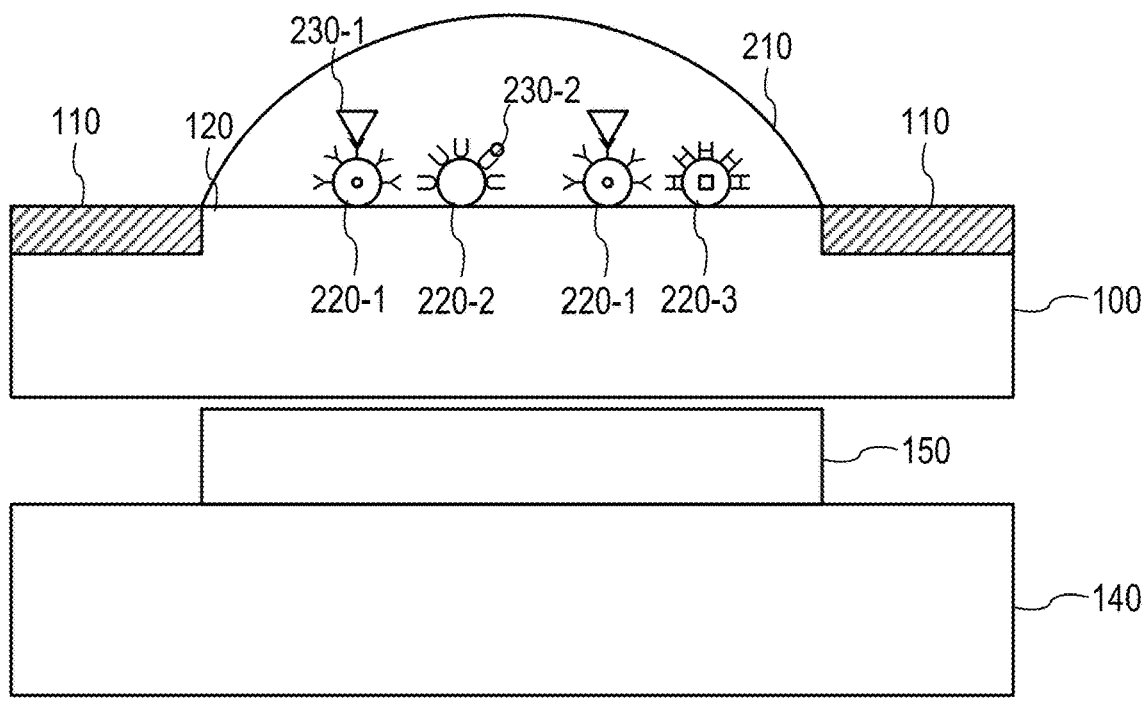

FIG. 2C illustrates that target molecules 230 that are not bound to magnetic components 220 are removed from sample solution 210 (e.g., by washing, including removing at least a portion of sample solution 210, and adding a washing solution to sample solution 210) and target molecules 230 that are bound to magnetic components 220 remain in sample solution 210.

Figure 2D:
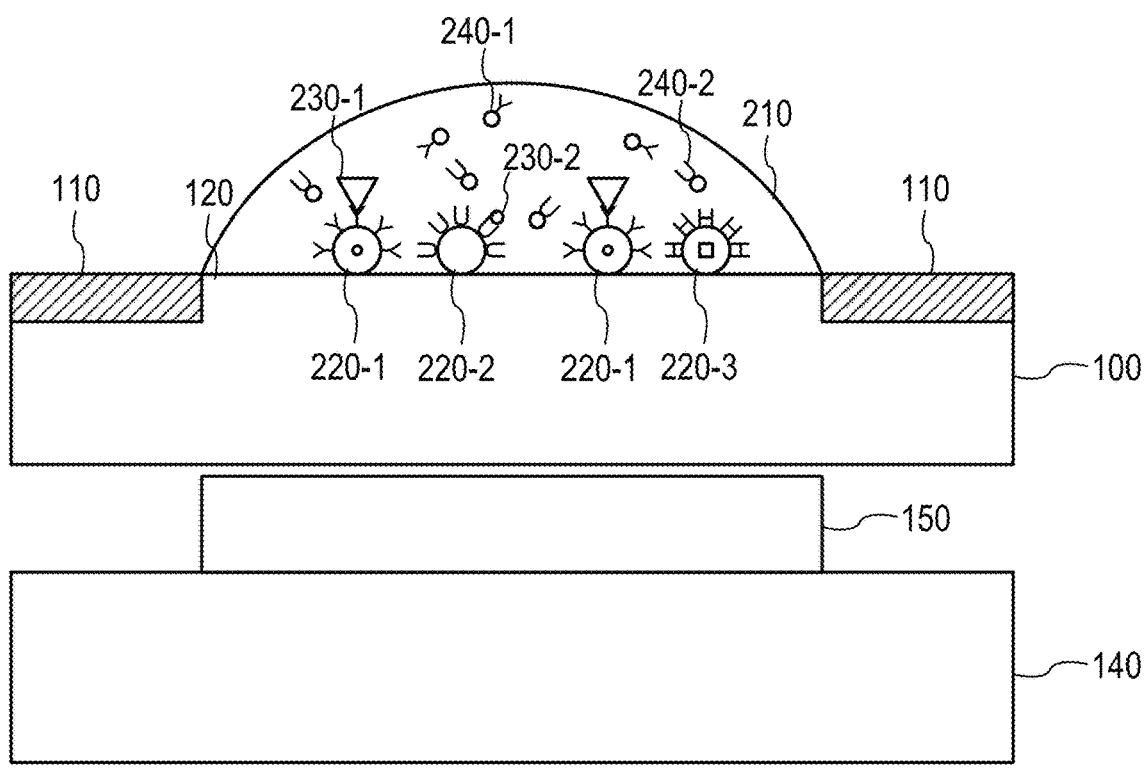

FIG. 2D illustrates that detection molecules 240 are added to sample solution 210. Detection molecule 240 includes a binding portion (e.g., detection antibody) that is configured to couple with target molecule 230. For example, detection molecule 240-1 is configured to couple with target molecule 230-1, and detection molecule 240-2 is configured to couple with target molecule 230-2. In some embodiments, detection molecules 240 include labels that emit light of particular wavelength patterns when illuminated with a light source. In some embodiments, detection molecules 240 are configured to couple with labels, but do not include labels.

Figure 2E:
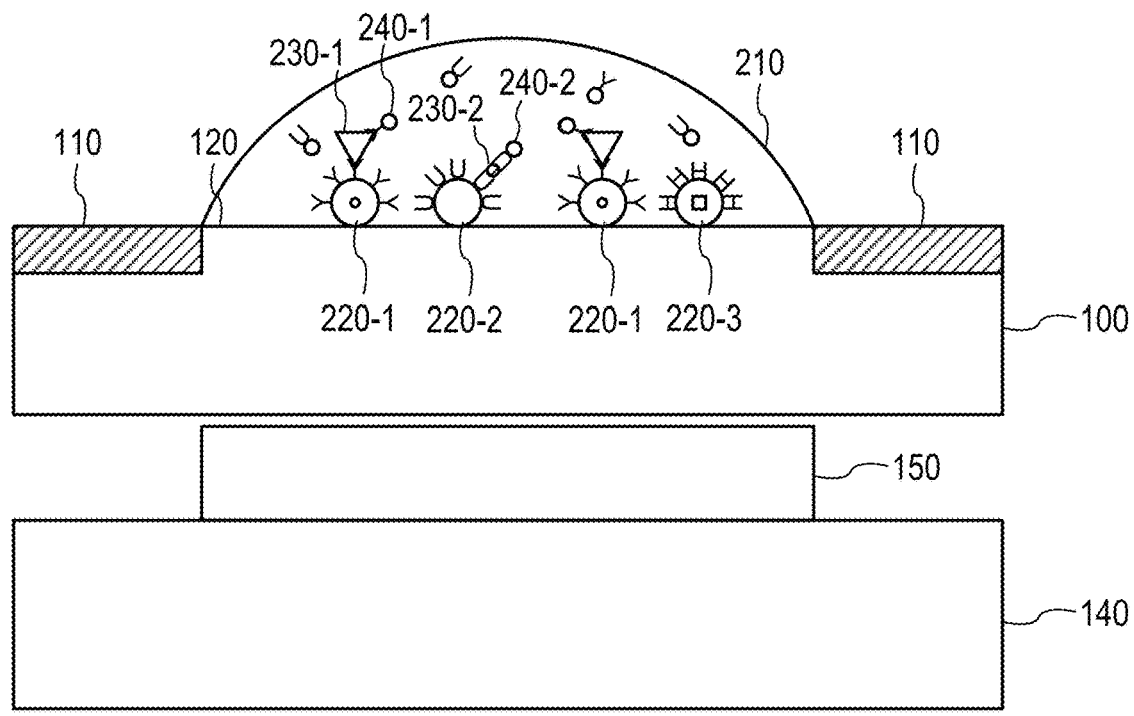

FIG. 2E illustrates that at least some of detection molecules 240 bind to target molecules 230.

Figure 2F:
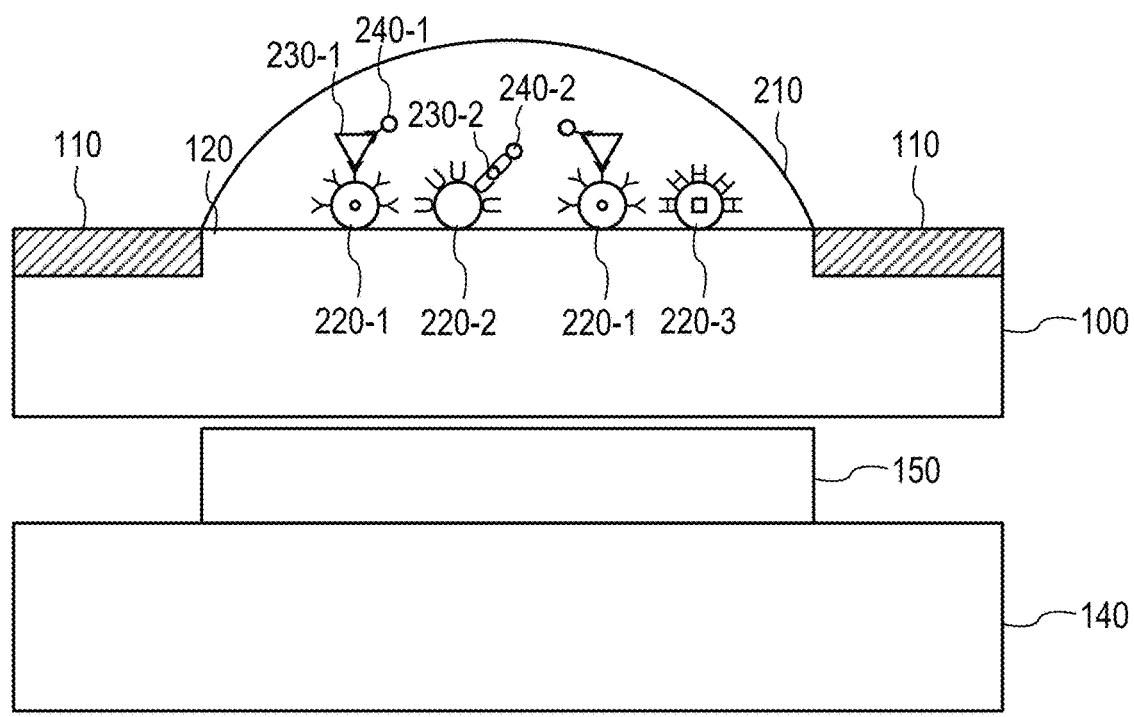

FIG. 2F illustrates that detection molecules 240 that are bound to target molecules 230 remain in sample solution 210 and detection molecules 240-2 that are not bound to target molecules 230 are removed from sample solution 210 (e.g., by washing, including removing at least a portion of sample solution 210, and adding a washing solution to sample solution 210, and, optionally repeating the removing and adding steps).

Figure 2G:
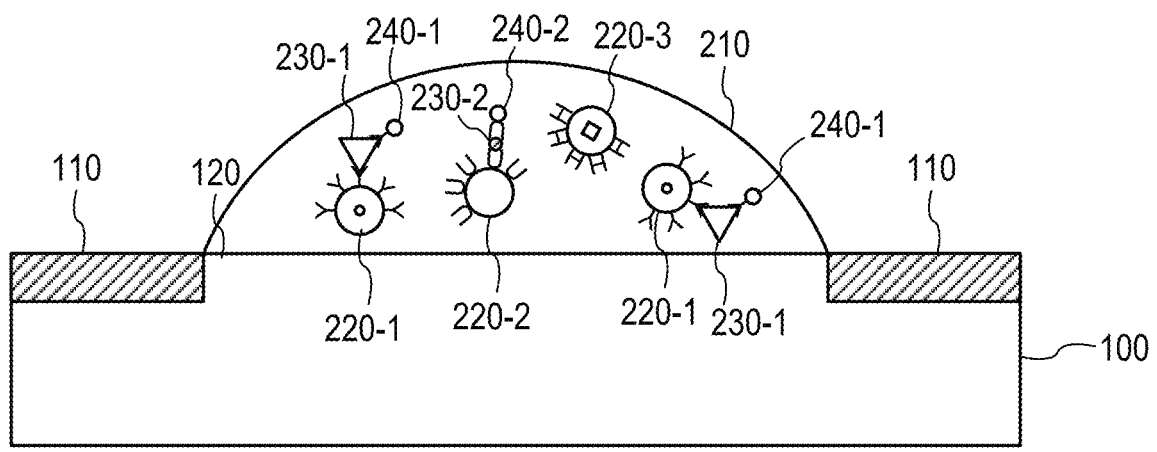

FIG. 2G illustrates that magnetic device plate 140 (shown in FIG. 2F) is moved away from array plate 100, and magnetic components 220 are released from the surface of array plate 100. In FIG. 2G, magnetic components 220 coupled with target molecules 230, which, in turn, are coupled with detection molecules 240, float in sample solution 210.

In some embodiments, a combination of magnetic component 220, target molecule 230, and detection molecule 240 is detected by optically scanning sample region 210. A combination of light emitted by detection molecule 240 and light emitted by magnetic component 220 indicates the presence of target molecule 230 that corresponds to both magnetic component 220 and detection molecule 240. For example, a combination of light emitted by detection molecule 240-1 and light emitted by magnetic component 220-1 indicates presence of target molecule 230-1, and a combination of light emitted by detection molecule 240-2 and light emitted by magnetic component 220-2 indicates presence of target molecule 230-2. In some embodiments, intensity of light emitted by detection molecules 240 indicates quantities of corresponding target molecules 230. For example, intensity of light emitted by detection molecule 240-1 indicates a quantity of target molecule 230-1, and intensity of light emitted by detection molecule 240-2 indicates a quantity of target molecule 230-2.

In some embodiments, a combination of magnetic component 220, target molecule 230, and detection molecule 240 is detected by using flow cytometry. In some embodiments, by flowing sample solution 210 through a flow cytometer, each combination of magnetic component 220, target molecule 230, and detection molecule 240 is separately detected.

Figure 2H:
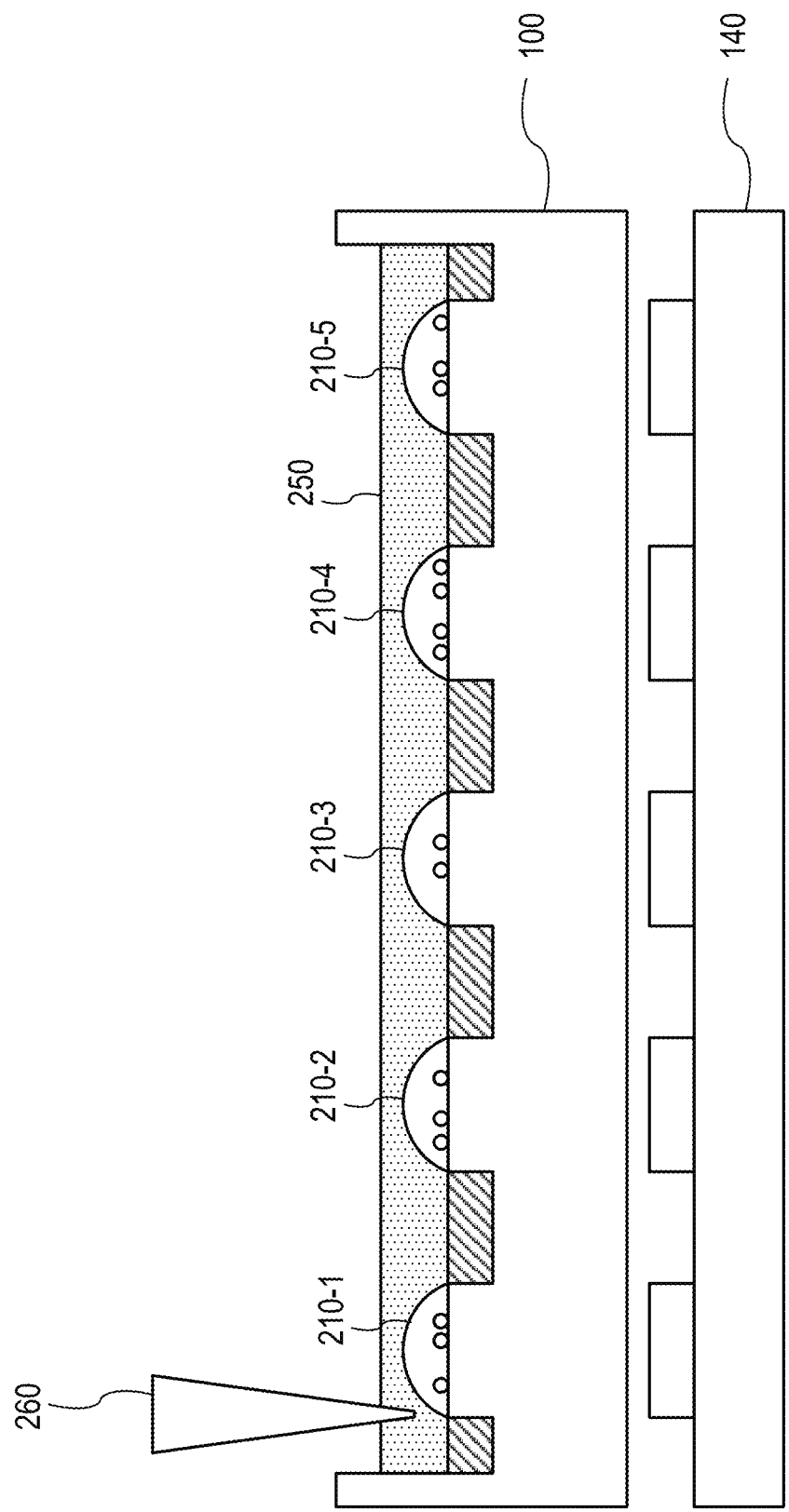
FIGS. 2H-2J are partial cross-sectional views of a system in accordance with some embodiments.

FIG. 2H illustrates that sample solutions 210-1 through 210-5 are covered with immiscible fluid 250 (e.g., perfluorocarbon liquid when sample solutions 210-1 through 210-5 are water-based). In some embodiments, immiscible fluid 250 reduces inter-mixing of sample solutions 210. Nozzle 260 (e.g., a tip of a pipette or a sipper) is positioned so that a tip of nozzle 260 is immersed in immiscible fluid 250. By moving nozzle 260 through sample solutions 210-1 through 210-5 (e.g., with a single, continuous, horizontal movement) while nozzle 260 continues to aspirate, sample solutions 210-1 through 210-5 are sequentially collected (and optionally, separated by immiscible fluid 250). The collected sample solutions 210-1 through 210-5 can be analyzed (e.g., by flowing the collected sample solutions through a flow cytometer) to determine the presence and quantities of target molecules in sample solutions 210-1 through 210-5. This method eliminates the need for exchanging pipette tips for removing samples from each sample solution 210, and allows rapid aspiration of sample solutions 210-1 through 210-5. In addition, continuous aspiration with nozzle 260 is compatible with continuous analysis using flow cytometry, therefore the integration of the sample collection with the flow cytometry analysis improves the throughput of bioassays.

In some embodiments, when eluates are needed for detection (e.g., when magnetic components interfere with detection of analytes), magnetic device plate 140 is placed in proximity to array plate 100 so that magnetic components are retained while eluates are aspirated by nozzle 260. In some embodiments, when a combination of a target molecule and a magnetic component (and optionally, a detection molecule) is needed for detection, magnetic device plate 140 is removed to release the combination so that the combination is aspirated by nozzle 260.

Figure 2I:
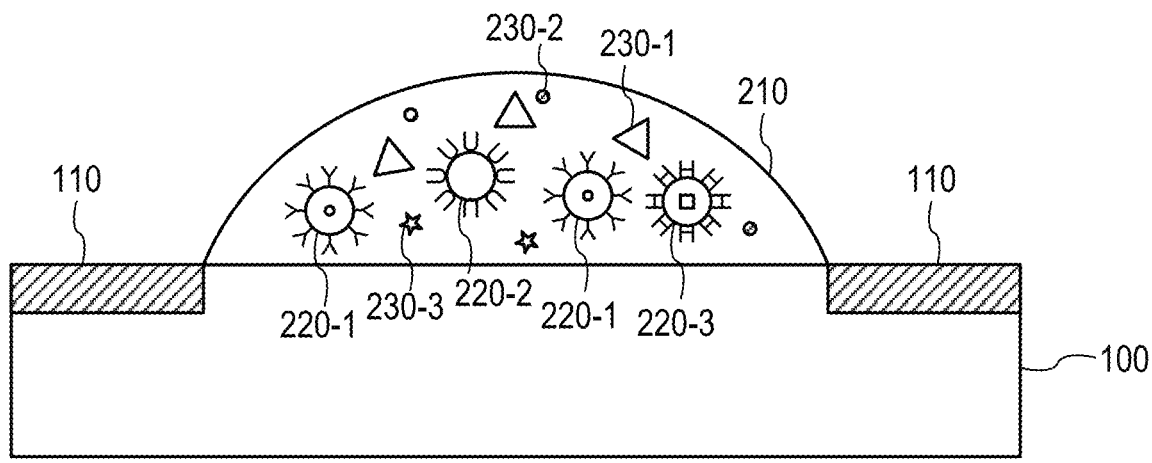
Figure 2J:
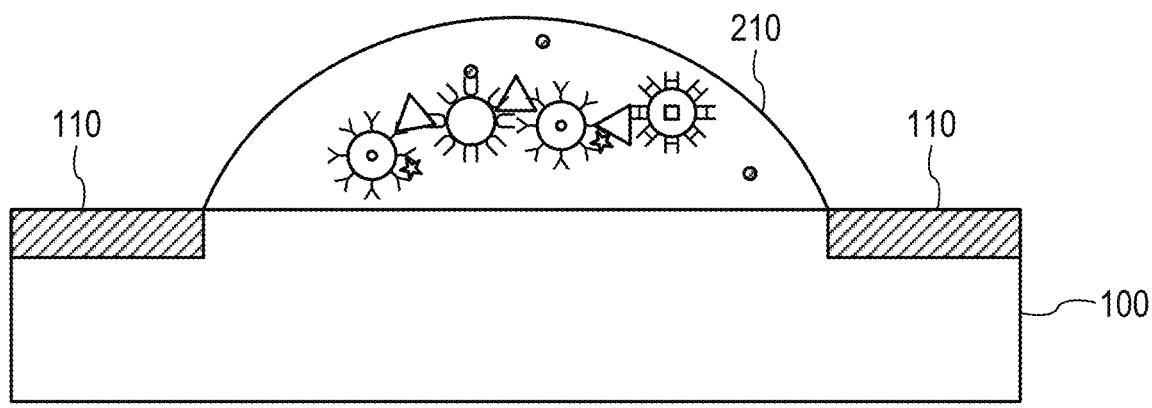

FIGS. 2I-2J are partial cross-sectional views of a system in accordance with some embodiments.

FIG. 2I illustrates that magnetic components 220 are free floating in sample solution 210 along with target molecules 230.

FIG. 2J illustrates that, in some cases, magnetic components 220 aggregate, thereby forming a lump of magnetic components 220. It has been discovered that when target molecules 230 include sticky molecules (e.g., sticky protein), the sticky molecules facilitate aggregation of magnetic components 220. Aggregation of magnetic components 220 reduces accuracy in detecting target molecules 230. For example, formation of an aggregate of magnetic components 220 blocks certain binding sites on magnetic components 220, thereby hindering binding of target molecules 230 with magnetic components 220. In addition, formation of an aggregate of magnetic components 220 blocks certain binding sites on target molecules 230, thereby hindering binding of target molecules 230 with detection molecules. Magnetic components 220 and/or target molecules 230 are trapped in the aggregate of magnetic components 220 reduce specificity in bioassays and increases background signal. Furthermore, an aggregate of magnetic components 220 is unsuitable for, and/or incompatible with, detection of magnetic components in some cases (e.g., certain detection methods require magnetic components 220 to be separated).

Thus, the problems associated with incubating free-floating magnetic components 220 with target molecules 230 are overcome by the methods described above with respect to FIGS. 2A-2H.

FIGS. 3A-3D are plan views of an array plate in accordance with some embodiments.

Figure 3A:
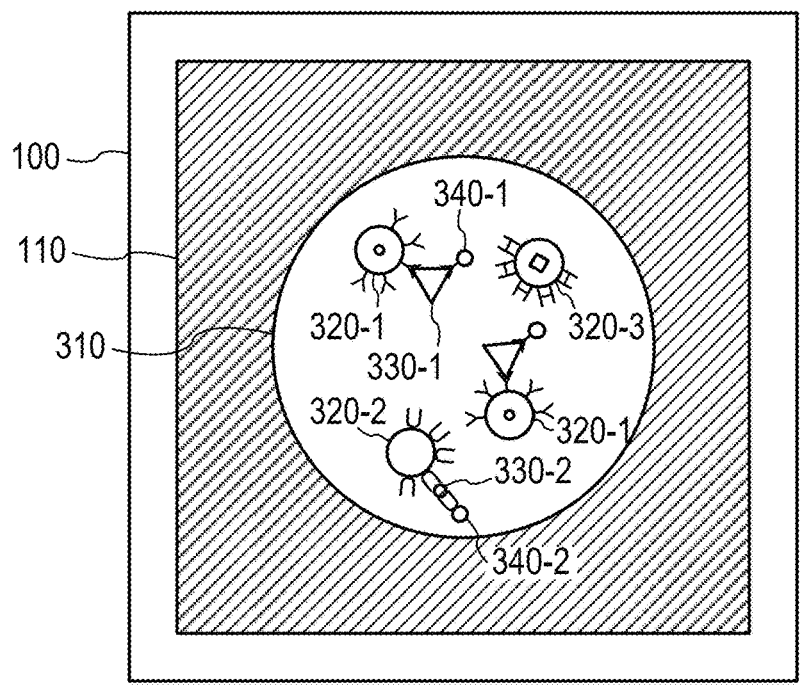
FIGS. 3A-3D are plan views of an array plate in accordance with some embodiments.

FIG. 3A illustrates that sample solution 310 is located on a sample region of array plate 100. Sample solution 310 includes a plurality of magnetic components 320 (e.g., 320-1, 320-2, and 320-3) configured to couple with respective target molecules 330. Sample solution 310 also includes target molecules 330 (e.g., 330-1 and 330-2) and detection molecules 340 (e.g., 340-1 and 340-2). In FIG. 3A, target molecule 330-1 is coupled with magnetic component 320-1 and detection molecule 340-1, and target molecule 330-2 is coupled with magnetic component 320-2 and detection molecule 340-2.

Figure 3B:
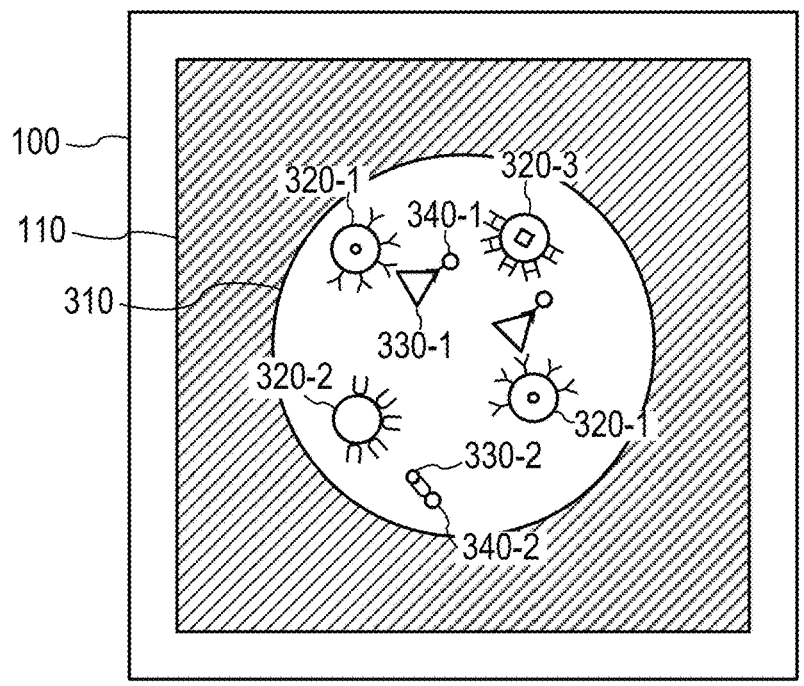

FIG. 3B illustrates that target molecule 330-1 is released from magnetic component 320-1 and target molecule 330-2 is released from magnetic component 320-2. In some embodiments, target molecules 330-1 and 330-2 are released from magnetic components 320-1 and 320-2 in response to adding an elution buffer to sample solution 310.

Certain detection methods require target molecules 330 (optionally coupled with detection molecules 340) without magnetic components 320. In conventional methods, separating target molecules 330 from magnetic components 320 requires aspirating at least a portion of sample solution 310 that includes at least a subset of target molecules 330 while magnetic components 320 are retained by one or more magnetic devices. However, such methods are time-consuming and inefficient. In addition, certain target molecules 330 are lost during aspiration of sample solution 310. Contamination of sample solution 310 is also possible. Furthermore, transferring sample solution 310 requires use of disposable pipette tips, which adds to costs of bioassays and increased wastes.

Figure 3C:
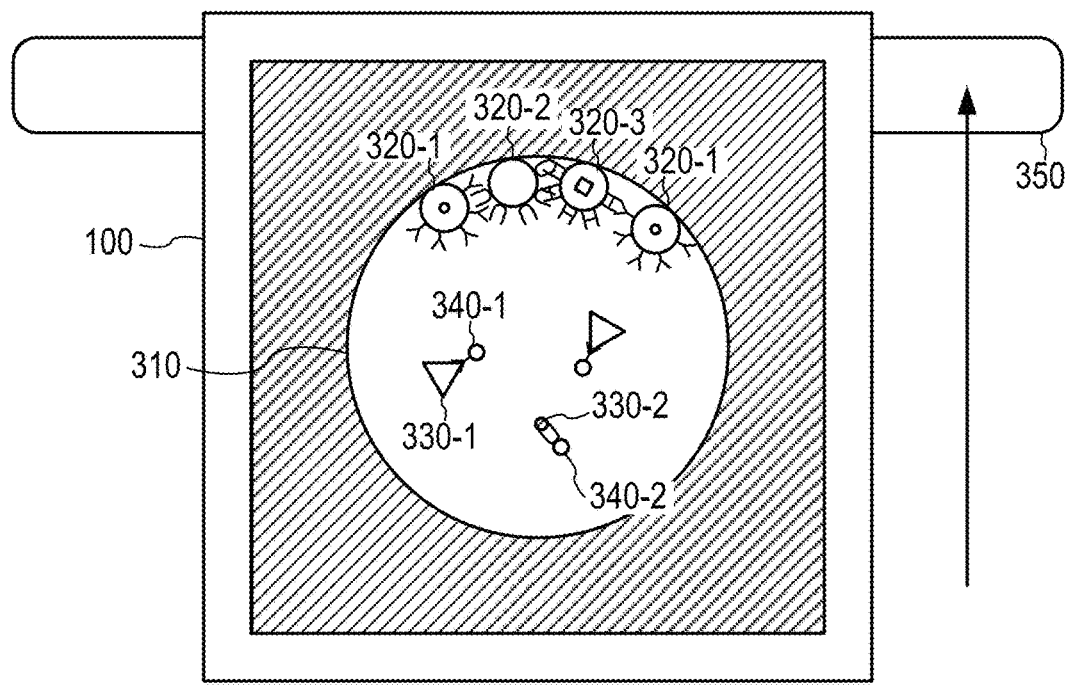

FIG. 3C shows that by placing magnetic device 350 (e.g., a permanent magnet) adjacent to sample solution 310 and passing magnetic device 350 by sample solution 310 (e.g., under sample solution 310) separates magnetic components 320 from target molecules 330. As shown in FIG. 3C, magnetic components 320 are located along one edge of sample solution 310 that is adjacent to magnetic device 350.

Figure 3D:
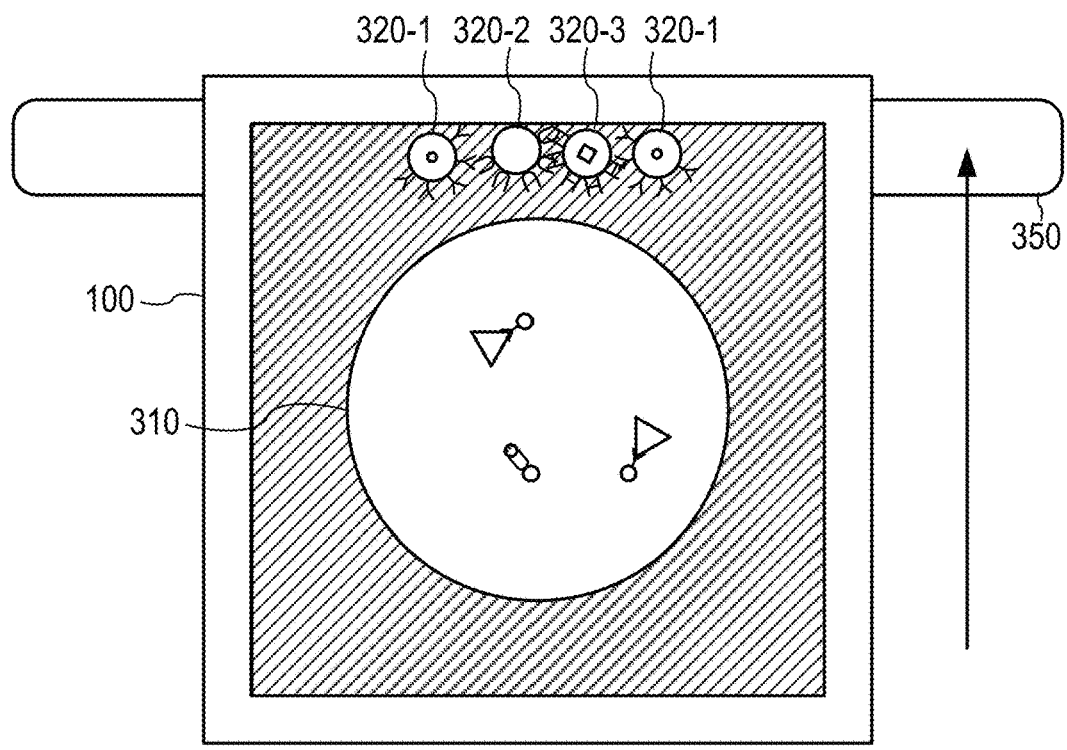

FIG. 3D shows that if magnetic device 350 provides a sufficient magnetic force (e.g., sufficient to overcome surface tension), magnetic components 320 are separated from sample solution 310. In some embodiments, sample solution 310 is agitated (e.g., shaken) while magnetic device 350 passes by sample solution 310 to facilitate the movement of magnetic components 320.

In some embodiments, subsequent to separating magnetic components 320 from sample solution 310, a second set of magnetic components (e.g., magnetic components different from those separated from sample solution 310) is added to sample solution 310 for subsequent processing (e.g., separation of a subset of target molecules). Such processing (e.g., disassociation and targeted retention) of target molecules can be repeated as needed. For brevity, such details are omitted herein.

Thus, FIGS. 3C-3D illustrate methods of spatially separating magnetic components 320 from target molecules 330 within a same sample solution. Such methods overcome limitations associated with conventional methods.

FIGS. 4A-4D are plan views of array plate 100 in accordance with some embodiments.

Figure 4A:
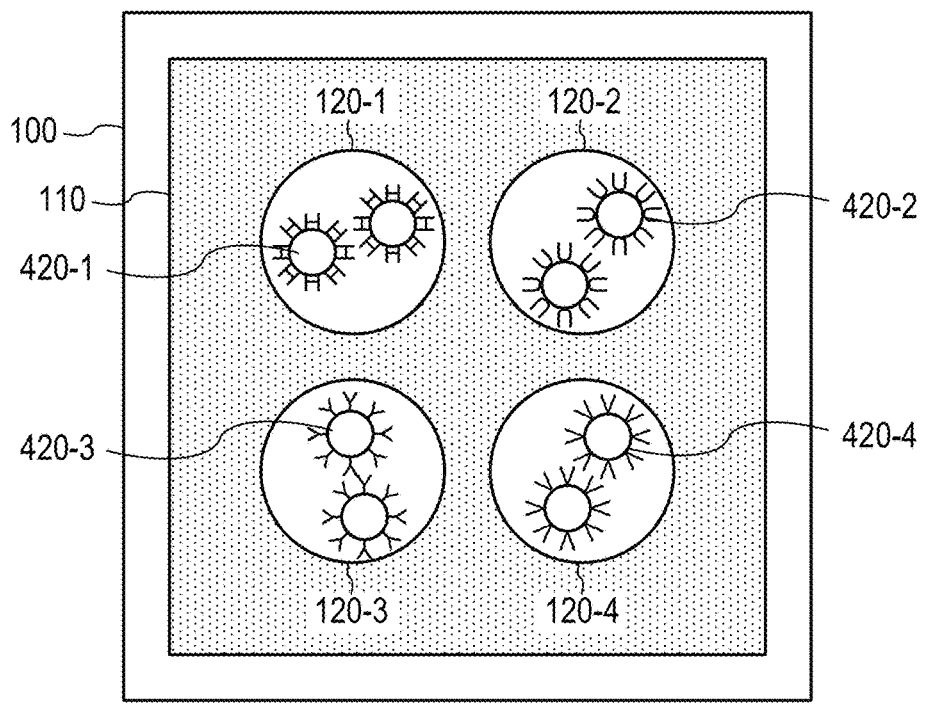
FIGS. 4A-4D are plan views of an array plate in accordance with some embodiments.

FIG. 4A illustrates that array plate 100 has multiple sample regions 120 (e.g., 120-1 through 120-4). In FIG. 4A, magnetic components 420-1 are located over sample region 120-1, magnetic components 420-2 are located over sample region 120-2, magnetic components 420-3 are located over sample region 120-3, and magnetic components 420-4 are located over sample region 120-4. For example, a solution that contains magnetic components 420-1 is dispensed over sample region 420-1. In FIG. 4A, the volume of the solution that contains magnetic components 420-1 is such that the solution does not come into contact with another sample region (e.g., 120-2 or 120-3). For example, for a sample region having a diameter of 2 mm, a solution volume between 1 µl and 3 µl may be used to deliver magnetic components.

In some embodiments, each sample region has a diameter of 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, or 26 mm. In some embodiments, sample regions within a same group are spaced apart. For example, sample regions having a diameter of 2 mm in a same group are spaced apart with 3 mm, 4 mm, or 5 mm pitch.

In some embodiments, a magnetic device plate (e.g., magnetic device plate 140 shown in FIG. 1A) is placed adjacent to array plate 100 to retain magnetic components 420. In some embodiments, the magnetic device plate remains adjacent to array plate 100 until magnetic components 420 need to be removed (e.g., for flow cytometry analysis). For example, the magnetic device plate remains adjacent to array plate 100 throughout operations illustrated in FIGS. 4A-4D and FIGS. 4E-4H.

Figure 4B:
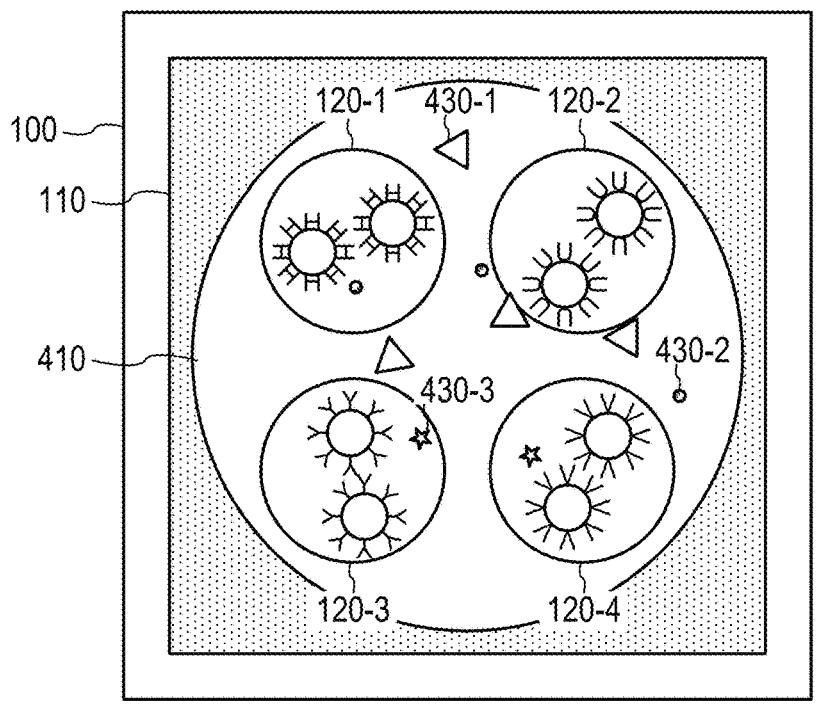

FIG. 4B illustrates that sample solution 410 is dispensed so that sample solution 410 comes in contact with sample regions 120-1, 120-2, 120-3, and 120-4. The volume of sample solution 410 is sufficient to contact sample regions 120-1, 120-2, 120-3, and 120-4. For example, a 2×2 array of sample regions each having a diameter of 2 mm, a sample solution having a volume between 10 µl to 25 µl is dispensed. Sample solution 410 includes target molecules 430. Surrounding region 110 reduces spreading of sample solution 410 (e.g., due to its hydrophobicity).

Figure 4C:
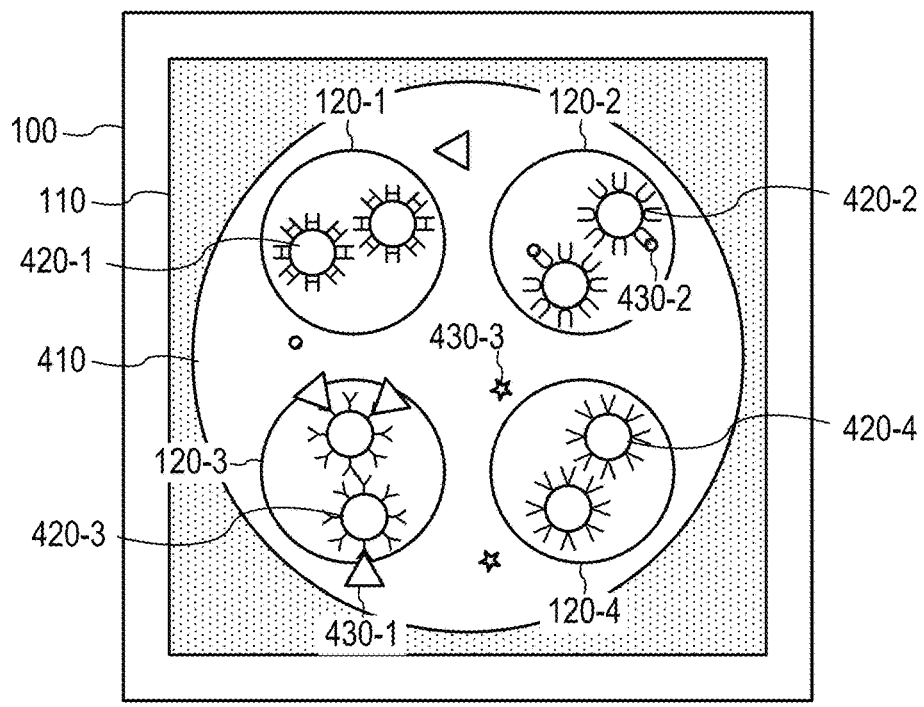

FIG. 4C illustrates that at least some target molecules 430 couple with magnetic components 420. For example, target molecule 430-1 couples with magnetic component 420-3, and target molecule 430-2 couples with magnetic component 420-2, in FIG. 4C.

Figure 4D:
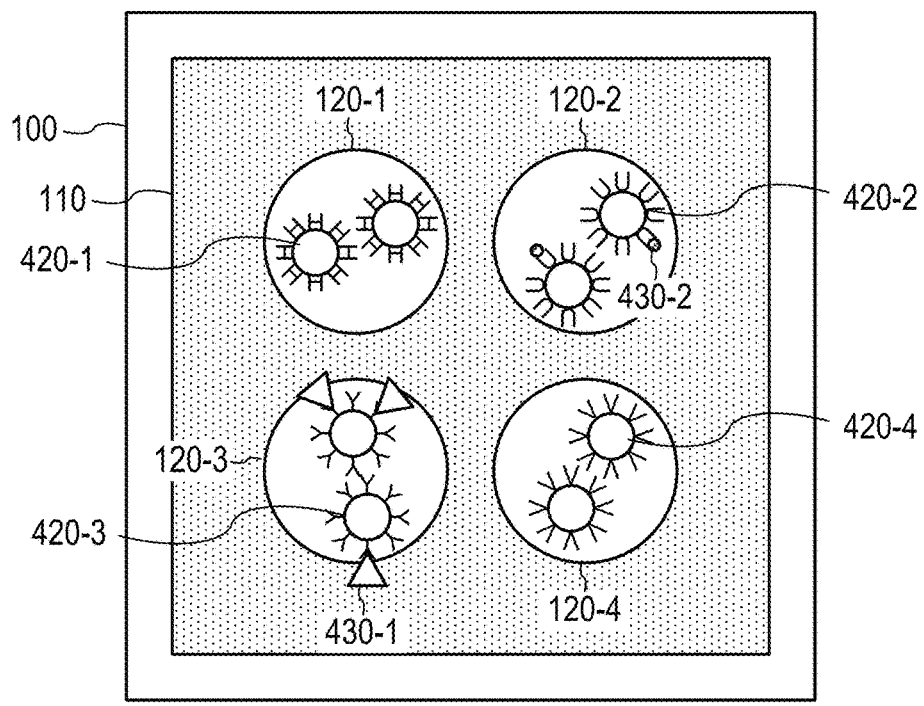

FIG. 4D illustrates that sample solution 410 is removed (e.g., through washing). Target molecules 430 that are bound with magnetic components 420 remain on array plate 100, and target molecules 430 that are not bound with magnetic components 420 are removed. Target molecules 430 that are bound with magnetic components 420 are detected. In some embodiments, detection molecules (e.g., detection molecules 240 in FIG. 2D) are used to detect target molecules 430 bound with magnetic components 420. In some embodiments, target molecules 430 are detected by optically scanning array plate 100. In some embodiments, target molecules 430 are detected by suspending target molecules 430 bound with magnetic components 420 by adding a buffer solution to respective sample regions 120 and analyzing the buffer solution with flow cytometry.

An array plate that includes hydrophilic regions and hydrophobic regions allows bioassays with a small sample volume (e.g., 5 µl or less). However, it is difficult to detect low concentration analytes in a small sample volume, when an average number of analytes in the sample volume approaches one or less. For example, when the sample solution with low analyte concentrations is divided into four droplets, due to molecule statistics, a droplet placed on sample region 120-1 may not include target molecules that can be detected by magnetic components on sample region 120-1 (or may not include sufficient target molecules that can be detected by magnetic components on sample region 120-1), whereas a droplet placed on sample region 120-2 may include target molecules that can be detected by magnetic components on sample region 120-1 (or may include sufficient target molecules that can be detected by magnetic components on sample region 120-1). By using a larger volume of the sample solution in a single droplet, instead of dividing the sample solution into four separate droplets, respective target molecules in sample solution 410 may move to sample regions 120-1, 120-2, 120-3, and 120-4 and bind with respective magnetic components configured to couple with the respective target molecules. Thus, the methods illustrated in FIGS. 4A-4D overcome this challenge.

FIGS. 4E-4H are plan views of an array plate in accordance with some embodiments.

Figure 4E:
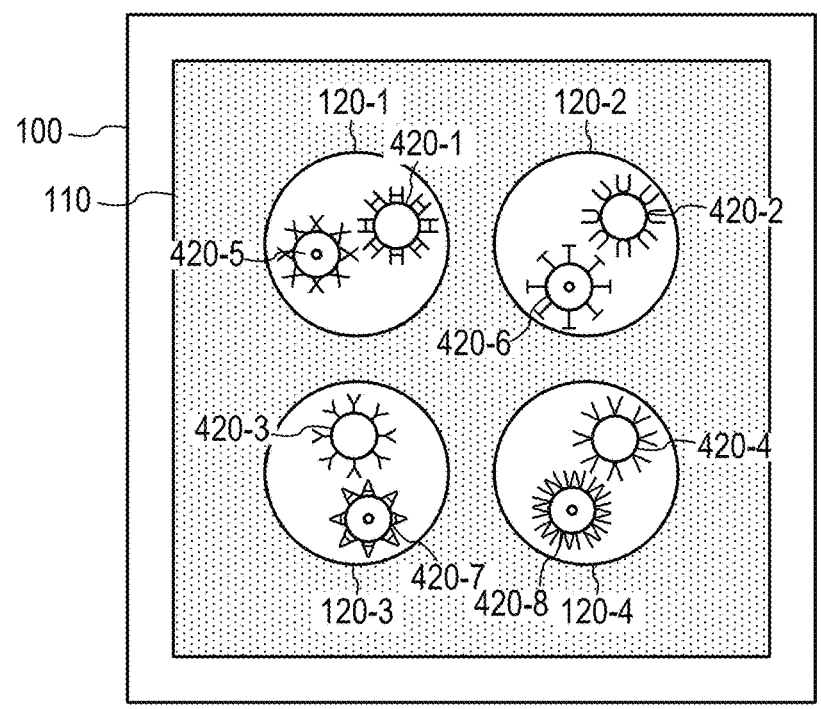
FIGS. 4E-4H are plan views of an array plate in accordance with some embodiments.

In FIG. 4E, sample region 120-1 includes magnetic component 420-1 configured to couple with a target molecule of a first type (e.g., target molecule 430-1 in FIG. 4E) and magnetic component 420-5 configured to couple with a target molecule of a fifth type. In some embodiments, magnetic component 420-1 and magnetic component 420-5 are placed on sample region 120-1 in a droplet that does not initially contact other sample regions (e.g., sample region 120-2, 120-3, and 120-4). Sample region 120-2 includes magnetic component 420-2 configured to couple with a target molecule of a second type (e.g., target molecule 430-2 in FIG. 4F) and magnetic component 420-6 configured to couple with a target molecule of a sixth type (e.g., target molecule 430-4 in FIG. 4F). Sample region 120-3 includes magnetic component 420-3 configured to couple with a target molecule of a third type and magnetic component 420-7 configured to couple with a target molecule of a seventh type. Sample region 120-4 includes magnetic component 420-4 configured to couple with a target molecule of a fourth type and magnetic component 420-8 configured to couple with a target molecule of an eighth type.

FIG. 4E illustrates that magnetic components 420-1, 420-2, 420-3, and 420-4 are associated with a first signal and magnetic components 420-5, 420-6, 420-7, and 420-8 are associated with a second signal that is distinct from the first signal. For example, magnetic components 420-1, 420-2, 420-3, and 420-4 emit light of a first wavelength pattern when illuminated by a light source, and magnetic components 420-5, 420-6, 420-7, and 420-8 emit light of a second wavelength pattern when illuminated by the light source. Therefore, magnetic components 420-1, 420-2, 420-3, and 420-4 can be distinguished from magnetic components 420-5, 420-6, 420-7, and 420-8 based on the wavelength pattern in the emitted light.

Figure 4F:
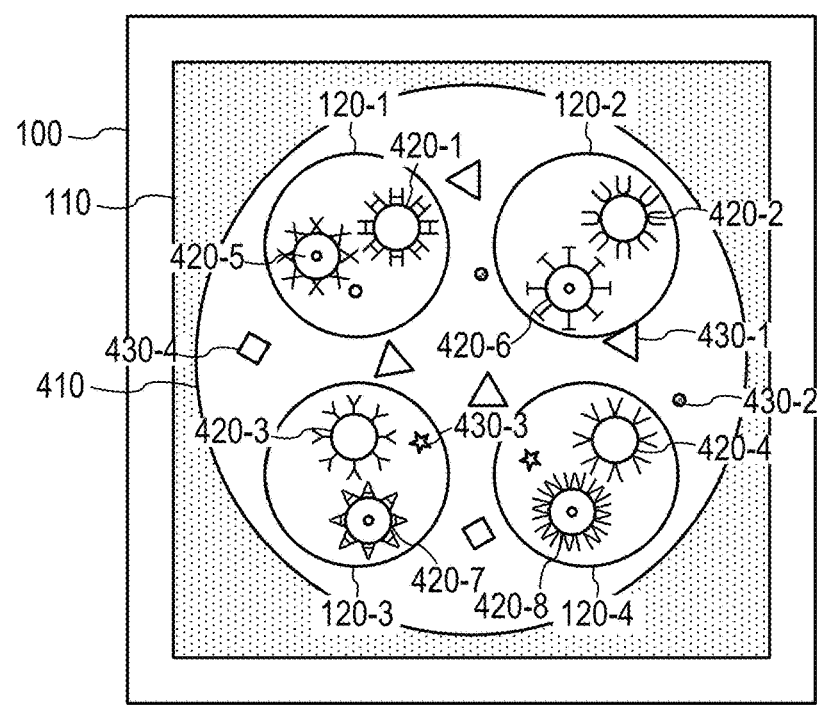

FIG. 4F illustrates that sample solution 410 is dispensed so that sample solution 410 comes in contact with sample regions 120-1, 120-2, 120-3, and 120-4. The volume of sample solution 410 is sufficient to contact sample regions 120-1, 120-2, 120-3, and 120-4. Sample solution 410 includes target molecules 430. Surrounding region 110 reduces spreading of sample solution 410 (e.g., due to its hydrophobicity).

Figure 4G:
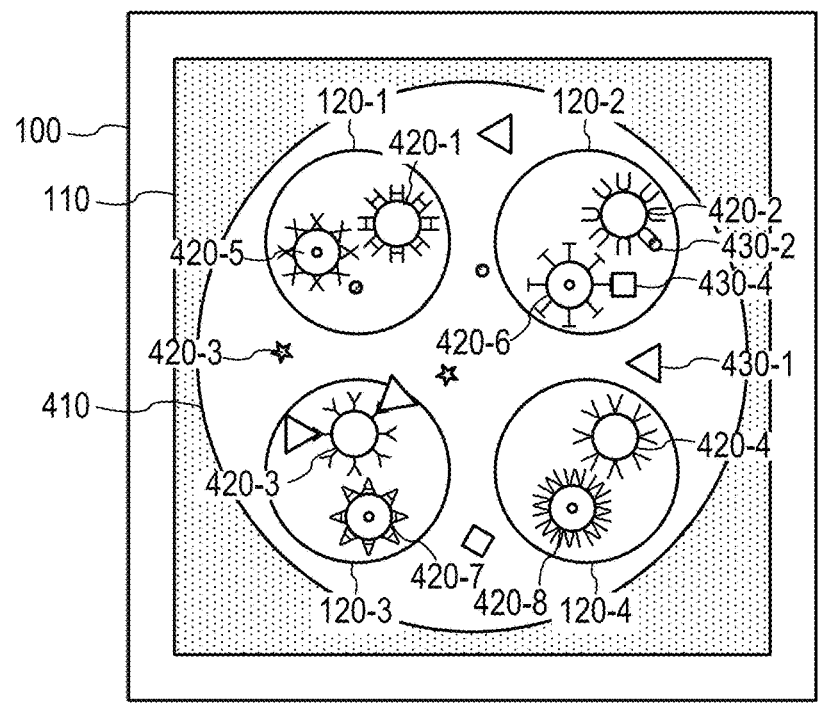

FIG. 4G illustrates that at least some target molecules 430 couple with magnetic components 420. For example, target molecule 430-1 couples with magnetic component 420-3, target molecule 430-2 couples with magnetic component 420-2, and target molecule 430-4 couples with magnetic component 420-6, in FIG. 4G.

Figure 4H:
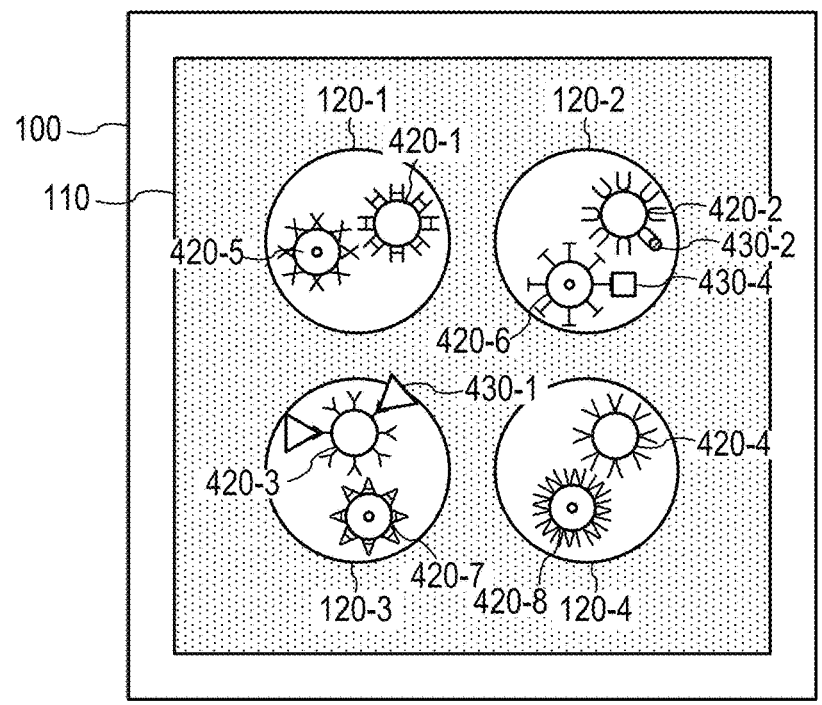

FIG. 4H illustrates that sample solution 410 is removed (e.g., through washing). Target molecules 430 that are bound with magnetic components 420 remain on array plate 100, and target molecules 430 that are not bound with magnetic components 420 are removed. Target molecules 430 that are bound with magnetic components 420 are detected. In some embodiments, detection molecules (e.g., detection molecules 240 in FIG. 2D) are used to detect target molecules 430 bound with magnetic components 420. In some embodiments, target molecules 430 are detected by optically scanning array plate 100. In some embodiments, target molecules 430 are detected by suspending target molecules 430 bound with magnetic components 420 by adding a buffer solution to respective sample regions 120 and analyzing the buffer solution with flow cytometry.

In FIGS. 4E-4H, magnetic components associated with two different signals (e.g., first and second wavelength patterns) are used. Because magnetic components are spatially separated, up to eight different analytes can be detected concurrently (e.g., 2 colors×4 wells=8 combinations). By increasing the number of sample regions and/or increasing the number of magnetic component types, an even larger number of analytes can be detected concurrently (e.g., 10 colors×16 wells=160 combinations). In addition, this reduces the requirement for a number of magnetic components with distinct colors (or wavelength patterns). Thus, this can simplify optical instruments for scanning array plate 100 or detecting magnetic components 420.

Figure 4I:
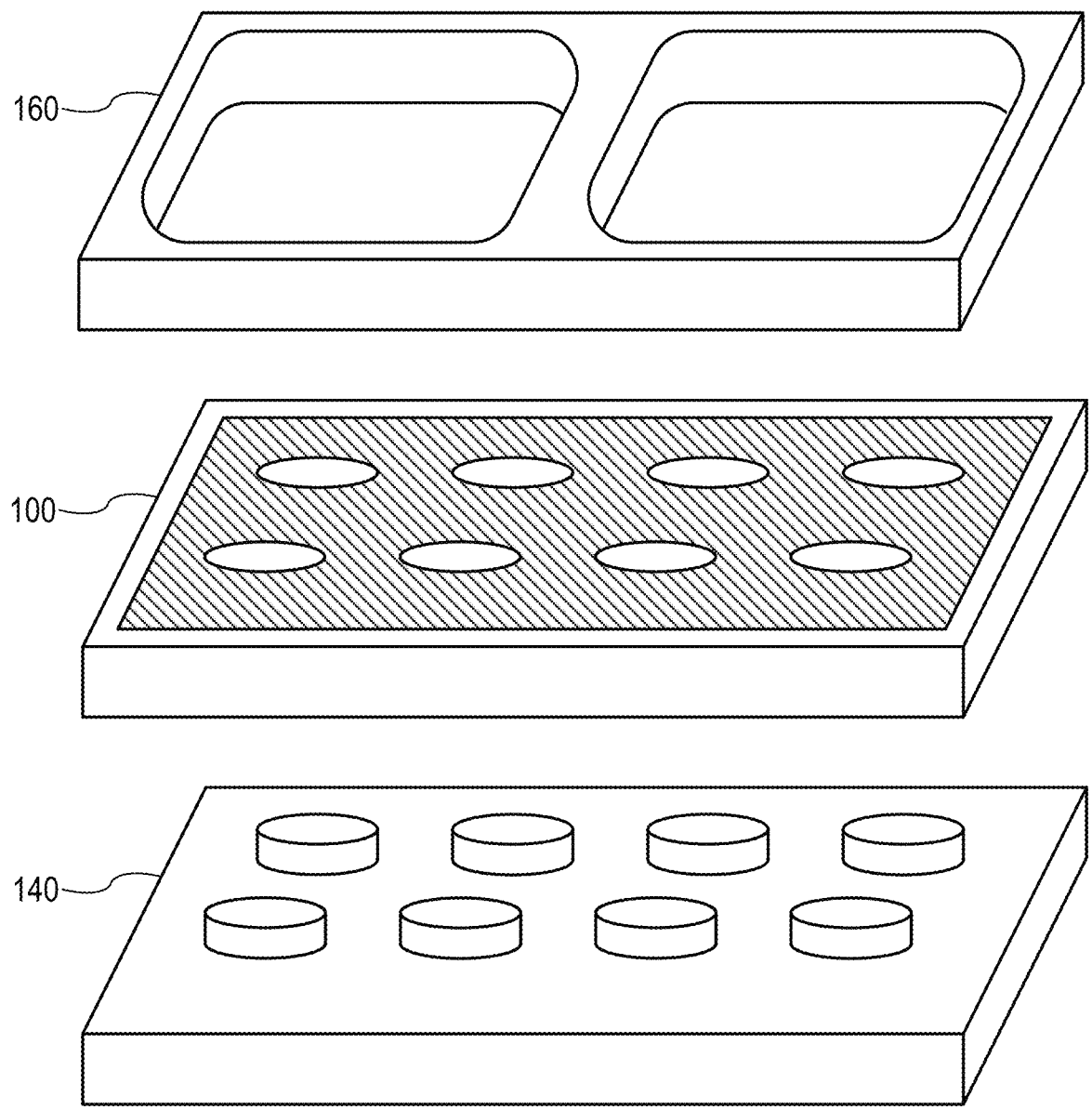
FIG. 4I is an exploded view of a system comprising an array plate, a magnetic device plate, and a grid in accordance with some embodiments.

FIG. 4I is an exploded view of a system comprising array plate 100, magnetic device plate 140, and grid 160 in accordance with some embodiments. In some embodiments, array plate 100 includes a thin layer of immiscible liquid (e.g., perfluorocarbon liquid) is applied. In some cases, the layer of immiscible liquid improves a seal between grid 160 and array plate 100. The combination of grid 160 and array plate 100 allows a larger volume of a sample solution to be placed on sample regions without spreading the sample solution.

Figure 4J:
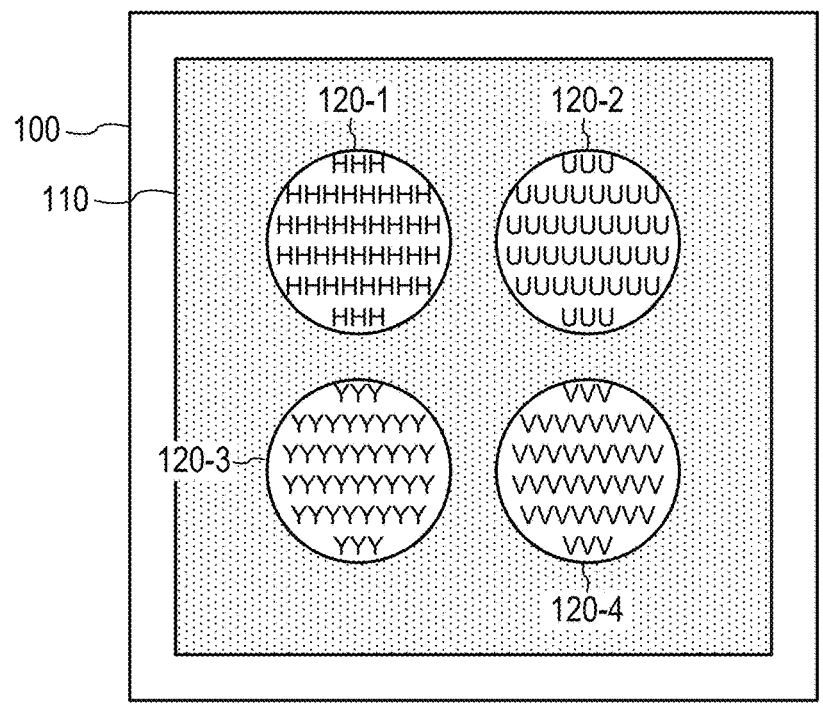
FIGS. 4J-4K are plan views of an array plate in accordance with some embodiments.
Figure 4K:
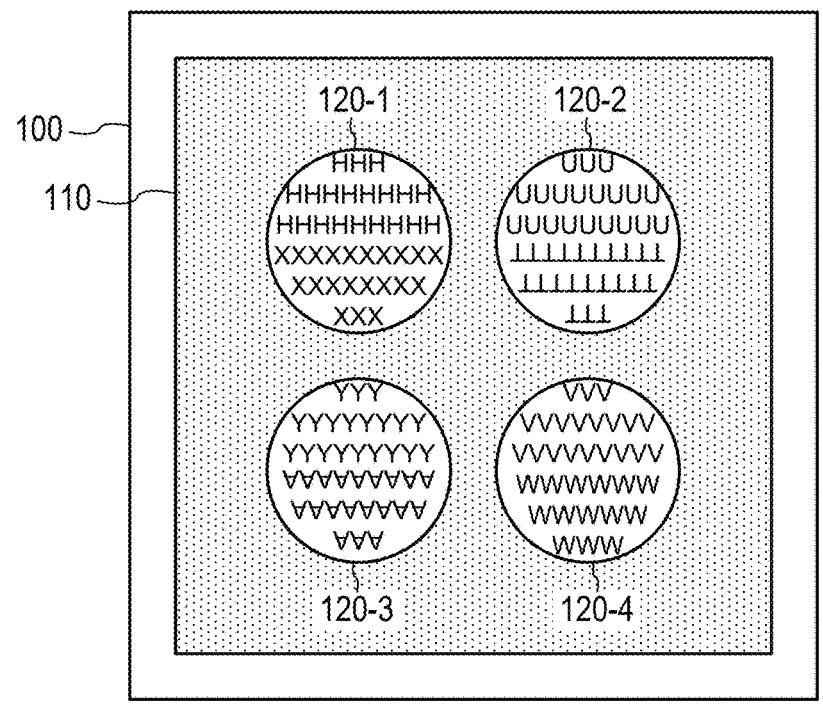

FIGS. 4J-4K are plan views of an array plate in accordance with some embodiments.

FIG. 4J illustrates that sample regions 120-1, 120-2, 120-3, and 120-4 are configured to couple with target molecules. In some embodiments, sample regions 120-1, 120-2, 120-3, and 120-4 are coated with capture molecules (e.g., antibodies, nucleic acid probes, etc.) for capturing (or coupling with) target molecules.

FIG. 4K illustrates that sample regions 120-1, 120-2, 120-3, and 120-4 are each coated with two different types of capture molecules. In FIG. 4K, sample region 120-1 includes capture molecules configured to couple with a target molecule of a first type and capture molecules configured to couple with a target molecule of a fifth type. Sample region 120-2 includes capture molecules configured to couple with a target molecule of a second type and capture molecules configured to couple with a target molecule of a sixth type. Sample region 120-3 includes capture molecules configured to couple with a target molecule of a third type and capture molecules configured to couple with a target molecule of a seventh type. Sample region 120-4 includes capture molecules configured to couple with a target molecule of a fourth type and capture molecules configured to couple with a target molecule of an eighth type. In some embodiments, target molecules captured in a sample region are eluted and subsequently analyzed (e.g., using magnetic components and/or detection molecules).

Although FIGS. 4A-4K illustrate the use of a group of four sample regions, a person having ordinary skill in the art would understand that more or fewer sample regions may be used as a group. For example, a group of two sample regions, a group of nine sample regions (3×3), or a group of sixteen sample regions (4×4) may be used. In some embodiments, all of the sample regions on an array plate is used as a single group. In some embodiments, two groups are spaced apart by 9 mm or 10 mm (e.g., center-to-center).

FIG. 5 is a flow diagram illustrating method 500 of obtaining target molecules bound to magnetic components in accordance with some embodiments.

Method 500 includes (502) obtaining an array plate with a sample surface that includes a plurality of sample regions and a surrounding region (e.g., array plate 100 in FIG. 1A). The plurality of sample regions has a first surface tension (e.g., the sample regions are hydrophilic). The surrounding region has a second surface tension. In some embodiments, the second surface tension is distinct from the first surface tension (e.g., the surrounding region is hydrophobic). In some embodiments, the first surface tension and the second surface tension are the same. A sample solution is located on a sample region of the plurality of sample regions (e.g., sample solution 210 in FIG. 2A). The sample solution includes a plurality of target molecules (e.g., target molecules 230 in FIG. 2A). The sample solution includes a plurality of magnetic components (e.g., magnetic components 220 in FIG. 2A, such as magnetic beads, magnetic particles, etc.), respective magnetic components of the plurality of magnetic components configured to couple with respective target molecules.

In some embodiments, the respective magnetic components have (504) respective signatures (e.g., optical signatures, such as fluorescence signals, absorption signals, Raman signals, etc.; electrical signatures, such as impedance, resistance, capacitance, etc.; magnetic signatures; etc.).

Method 500 also includes (506) incubating the sample solution while one or more magnetic devices are positioned adjacent to the sample solution (e.g., FIG. 2B).

In some embodiments, method 500 includes (508) agitating the sample solution while incubating the sample solution. For example, the sample solution is vortexed every 5 minutes while incubating the sample solution.

In some embodiments, method 500 includes (509) incubating the sample solution without agitating the sample solution. For example, the sample solution is first agitated (e.g., vortexed), and subsequently incubated without further agitation (e.g., the sample solution is left stationary without further vortexing).

In some embodiments, method 500 includes placing a lid over the array plate while the sample solution is incubated. This reduces evaporation of the sample solution during the incubation.

Method 500 further includes (510) washing the plurality of magnetic components to obtain target molecules bound to at least a subset of the plurality of magnetic components (e.g., FIG. 2C).

In some embodiments, method 500 includes (512) detecting the target molecules bound to at least the subset of the plurality of magnetic components. For example, the target molecules can be optically scanned on array plate 100 or extracted for flow cytometry analysis, with or without using detection molecules.

In some embodiments, method 500 includes (514) adding to the sample solution a plurality of detection molecules configured to couple with the respective target molecules (e.g., detection molecules 240 in FIG. 2D).

In some embodiments, method 500 includes (516) washing the plurality of magnetic components to obtain target molecules bound to at least a subset of the plurality of magnetic components and at least a subset of the plurality of detection molecules (e.g., FIG. 2F).

In some embodiments, method 500 includes (518) detecting a combination of a respective target molecule coupled with a respective magnetic component and a respective detection molecule. For example, the target molecules can be optically scanned on array plate 100 or extracted for flow cytometry analysis.

It should be understood that the particular order in which the operations in FIG. 5 have been described is merely exemplary and is not intended to indicate that the described order is the only order in which the operations could be performed. One of ordinary skill in the art would recognize various ways to reorder the operations described herein. In some implementations, one or more operations described herein may be omitted. Additionally, it should be noted that details of other processes described herein with respect to other methods described herein (e.g., methods 600, 700, and 900) are also applicable in an analogous manner to method 500 described above with respect to FIG. 5. For example, the sample regions, sample solutions, magnetic components, and target molecules, described above with reference to method 500 optionally have one or more of the characteristics of the sample regions, sample solutions, magnetic components, and target molecules described herein with reference to other methods described herein (e.g., methods 600, 700, and 900). For brevity, these details are not repeated here.

Figure 6:
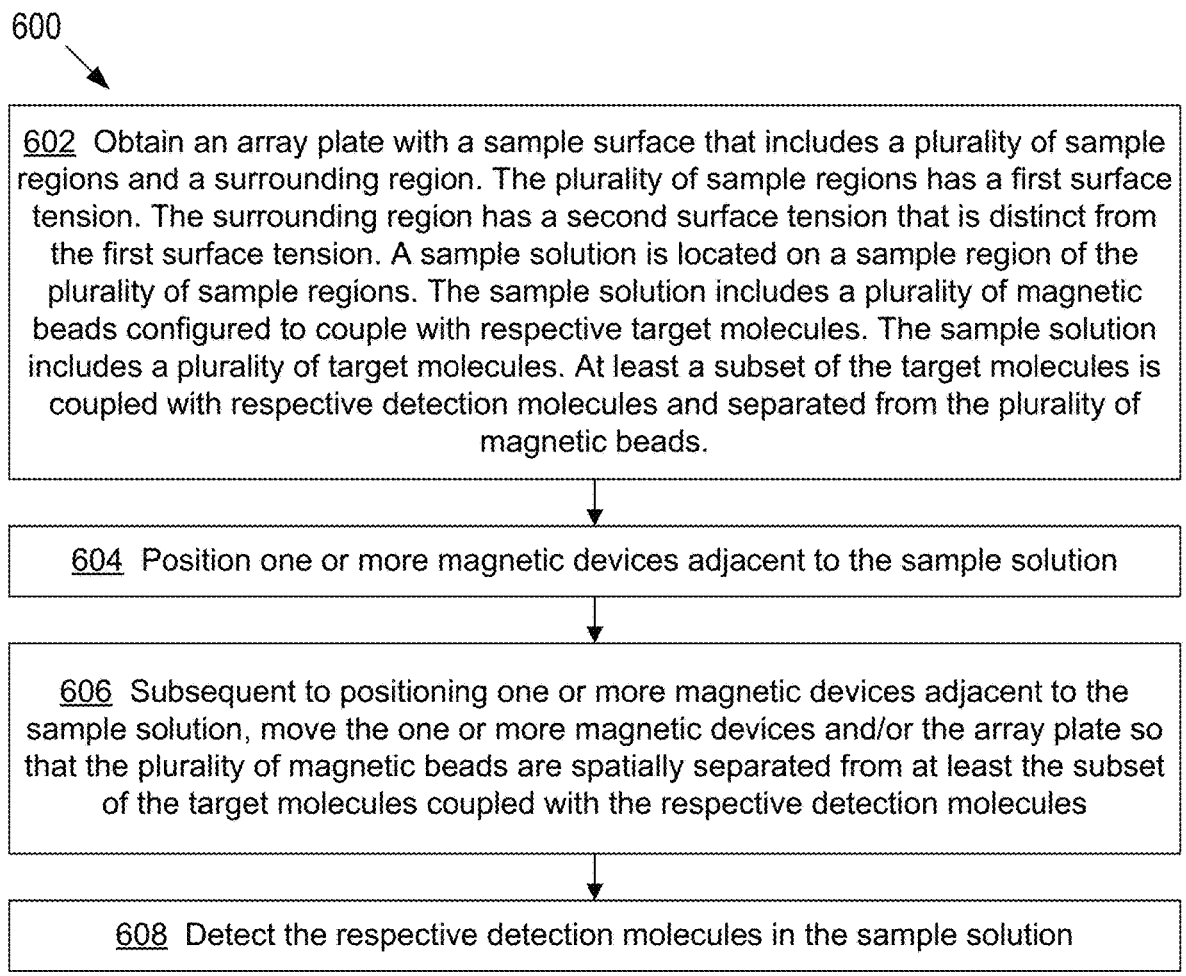
FIG. 6 is a flow diagram illustrating a method of detecting target molecules in accordance with some embodiments.

FIG. 6 is a flow diagram illustrating method 600 of detecting target molecules in accordance with some embodiments.

Method 600 includes (602) obtaining an array plate with a sample surface that includes a plurality of sample regions and a surrounding region (e.g., array plate 100 in FIG. 3B with a sample region surrounded by surrounding region 110). The plurality of sample regions has a first surface tension (e.g., hydrophilic). The surrounding region has a second surface tension. In some embodiments, the second surface tension is distinct from the first surface tension (e.g., the surrounding region is hydrophobic). In some embodiments, the first surface tension and the second surface tension are the same. A sample solution is located on a sample region of the plurality of sample regions (e.g., sample solution 310 in FIG. 3B). The sample solution includes a plurality of magnetic components configured to couple with respective target molecules (e.g., magnetic components 320 in FIG. 3B). The sample solution includes a plurality of target molecules, at least a subset of the target molecules coupled with respective detection molecules and separated from the plurality of magnetic components (e.g., target molecules 330 and magnetic components 320 in FIG. 3B).

Method 600 also includes (604) positioning one or more magnetic devices adjacent to the sample solution, and, subsequent to positioning one or more magnetic devices adjacent to the sample solution, (606) moving the one or more magnetic devices and/or the array plate so that the plurality of magnetic components are spatially separated from at least the subset of the target molecules coupled with the respective detection molecules (e.g., FIG. 3C or FIG. 3D).

Method 600 further includes (608) detecting the respective detection molecules in the sample solution.

It should be understood that the particular order in which the operations in FIG. 6 have been described is merely exemplary and is not intended to indicate that the described order is the only order in which the operations could be performed. One of ordinary skill in the art would recognize various ways to reorder the operations described herein. In some implementations, one or more operations described herein may be omitted. Additionally, it should be noted that details of other processes described herein with respect to other methods described herein (e.g., methods 500, 700, and 900) are also applicable in an analogous manner to method 600 described above with respect to FIG. 6. For example, the sample regions, sample solutions, magnetic components, and target molecules, described above with reference to method 600 optionally have one or more of the characteristics of the sample regions, sample solutions, magnetic components, and target molecules described herein with reference to other methods described herein (e.g., methods 500, 700, and 900). For brevity, these details are not repeated here.

FIG. 7 is a flow diagram illustrating method 700 of obtaining target molecules bound to magnetic components in accordance with some embodiments.

Method 700 includes (702) obtaining an array plate with a sample surface that includes a plurality of sample regions and a surrounding region (e.g., array plate 100 in FIG. 4E). The plurality of sample regions has a first surface tension. The surrounding region has a second surface tension. In some embodiments, the second surface tension is distinct from the first surface tension. In some embodiments, the first surface tension and the second surface tension are the same. A first sample region of the plurality of sample regions has a first set of magnetic components each configured to couple with a target molecule of a first type (e.g., in FIG. 4E, sample region 120-2 has magnetic component 420-3 that is configured to couple with target molecule 430-2). A second sample region of the plurality of sample regions has a second set of magnetic components each configured to couple with a target molecule of a second type that is distinct from a target molecule of the first type (e.g., sample region 120-3 has magnetic component 420-3 that is configured to couple with target molecule 430-1).

In some embodiments, the first sample region of the plurality of sample regions has (704) a third set of magnetic components each configured to couple with a target molecule of a third type that is distinct from a target molecule of the first type and a target molecule of the second type (e.g., in FIG. 4E, sample region 120-2 has magnetic component 420-6 that is configured to couple with target molecule 430-4 that is distinct from target molecule 430-1 and target molecule 430-2); and the second sample region of the plurality of sample regions has a fourth set of magnetic components each configured to couple with a target molecule of a fourth type that is distinct from a target molecule of the first type, a target molecule of the second type, and a target molecule of the third type (e.g., sample region 120-3 has magnetic component 420-7 that is configured to couple with a target mole that is distinct from target molecule 430-1, target molecule 430-2, and target molecule 430-4).

In some embodiments, the first set of magnetic components is associated (706) with a first signal; the second set of magnetic components is associated with a second signal that is distinct from the first signal; the third set of magnetic components is associated with a third signal; and the fourth set of magnetic components is associated with a fourth signal that is distinct from the third signal. For example, in FIG. 4E, magnetic bead 420-2 and magnetic bead 420-6 emit different wavelength patterns when illuminated with a light source, and magnetic bead 420-3 and magnetic 420-7 emit different wavelength patterns when illuminated with the light source.

In some embodiments, the third signal is identical (708) to either the first signal or the second signal. For example, in FIG. 4E, magnetic bead 420-3 and magnetic bead 420-3 emit the same wavelength pattern when illuminated with the light source.

In some embodiments, as shown in FIG. 4E, magnetic components 420-2 and magnetic components 420-3 emit a first wavelength pattern when illuminated with a light source, and magnetic components 420-6 and magnetic components 420-7 emit a second wavelength pattern when illuminated with the light source (e.g., magnetic components 420-2 and magnetic components 420-3 have the same color, and magnetic components 420-6 and magnetic components 420-7 have the same color that is distinct from the color of magnetic components 420-2 and magnetic components 420-3).

Method 700 includes (710) positioning one or more magnetic devices adjacent to the first sample region and the second sample region to retain the magnetic components on the first sample region and the second sample region (e.g., FIG. 1B).

Method 700 includes (712) providing a sample solution over multiple sample regions, including the first sample region and the second sample region, of the plurality of sample regions so that a single contiguous volume of the sample solution is in contact with the multiple sample regions, including the first sample region and the second sample region, while the magnetic components on the first sample region and the second sample region are retained by the one or more magnetic devices (e.g., sample solution 410 in FIG. 4F).

Method 700 includes (714) incubating the sample solution while one or more magnetic devices are positioned adjacent to the first sample region and the second sample region (e.g., some of target molecules 430 bind to at least a subset of magnetic components 420 in FIG. 4G).

Method 700 includes (716) washing the magnetic components to obtain target molecules bound to at least a subset of the magnetic components on the first sample region and/or the second sample region (e.g., FIG. 4H). In some embodiments, the target molecules bound to magnetic components are analyzed to detect the presence and/or quantities of the target molecules (e.g., through optical scanning and/or flow cytometry), with or without detection molecules.

It should be understood that the particular order in which the operations in FIG. 7 have been described is merely exemplary and is not intended to indicate that the described order is the only order in which the operations could be performed. One of ordinary skill in the art would recognize various ways to reorder the operations described herein. In some implementations, one or more operations described herein may be omitted. Additionally, it should be noted that details of other processes described herein with respect to other methods described herein (e.g., methods 500, 600, and 900) are also applicable in an analogous manner to method 700 described above with respect to FIG. 7. For example, the sample regions, sample solutions, magnetic components, and target molecules, described above with reference to method 700 optionally have one or more of the characteristics of the sample regions, sample solutions, magnetic components, and target molecules described herein with reference to other methods described herein (e.g., methods 500, 600, and 900). For brevity, these details are not repeated here.

FIGS. 8A-8H illustrate a method of transferring magnetic components from a solution in accordance with some embodiments.

Figure 8A:
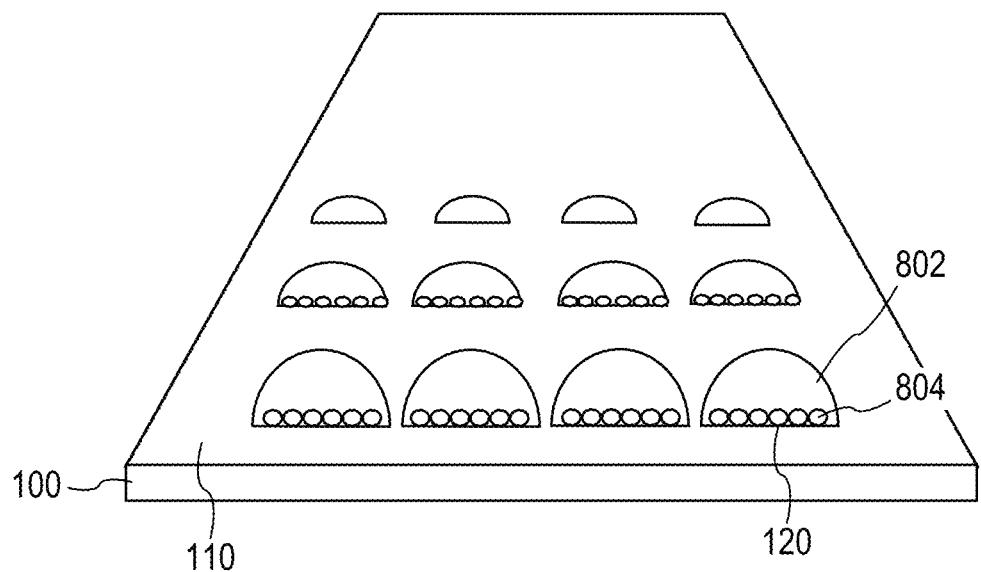
FIGS. 8A-8H illustrate a method of transferring magnetic components from a solution in accordance with some embodiments.

FIG. 8A illustrates array plate 100 that includes a plurality of sample regions 120 and surrounding region 110. In some embodiments, the plurality of sample regions 120 has a first surface tension (e.g., sample region 120 is hydrophilic); and surrounding region 110 has a second surface tension that is distinct from the first surface tension (e.g., surrounding region 110 is hydrophobic).

In FIG. 8A, first solution 802 (e.g., a sample solution) is located on sample region 120. First solution 802 includes a plurality of magnetic components 804. In some embodiments, the first solution includes a plurality of target molecules; and respective magnetic components of the plurality of magnetic components are configured to couple with respective target molecules. In some embodiments, the respective magnetic components are coupled with respective target molecules (e.g., see FIG. 2C). In some embodiments, the first solution includes a plurality of detection molecules, and respective detection molecules are coupled with target molecules (e.g., see FIG. 2F).

Figure 8B:
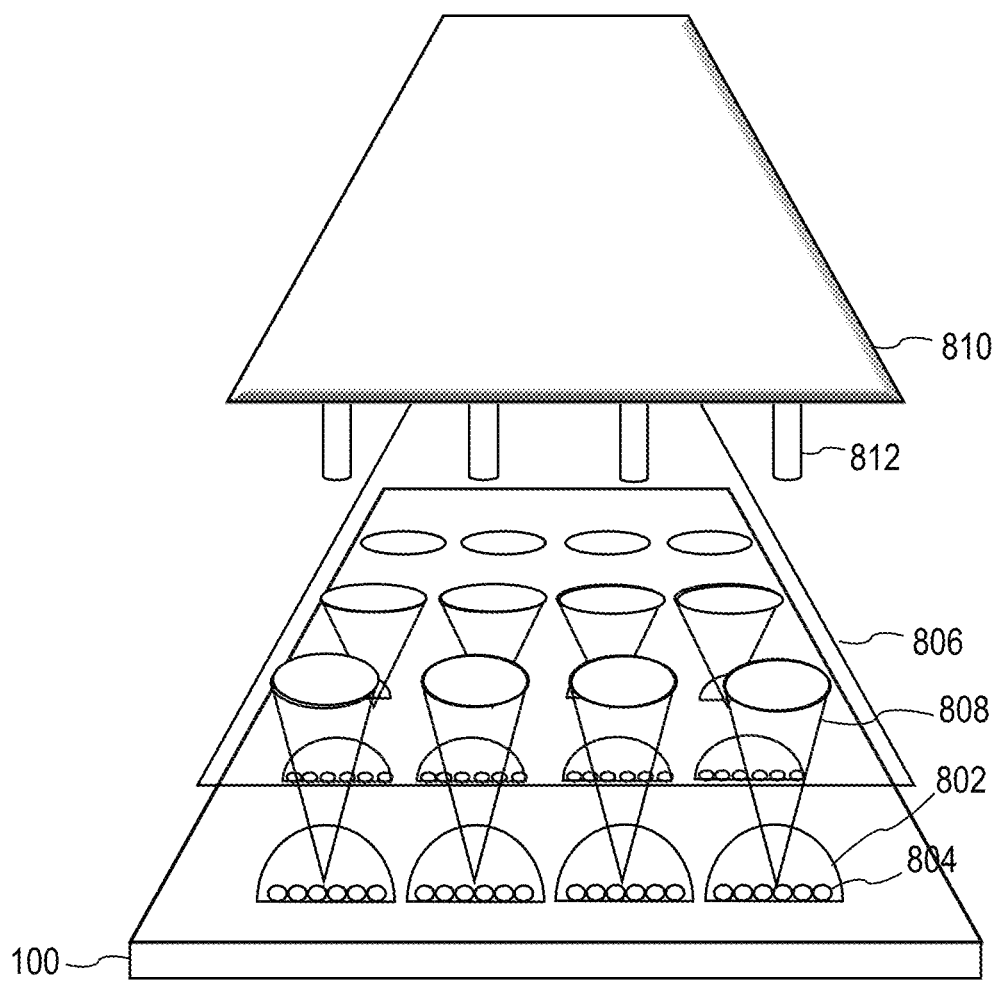

FIG. 8B illustrates that separation layer 806 (e.g., a polymerase chain reaction (PCR) plate, such as a non-skirted (or skirtless) PCR plate) is placed over array plate 100. Separation layer 806 includes one or more protrusions 808 (e.g., indentations defining wells). In FIG. 8B, protrusion 808 is in contact with first solution 802 (e.g., at least a portion of protrusion 808 is immersed in first solution 802).

FIG. 8B also illustrates magnetic pin array 810 with a plurality of magnetic pins 812.

Figure 8C:
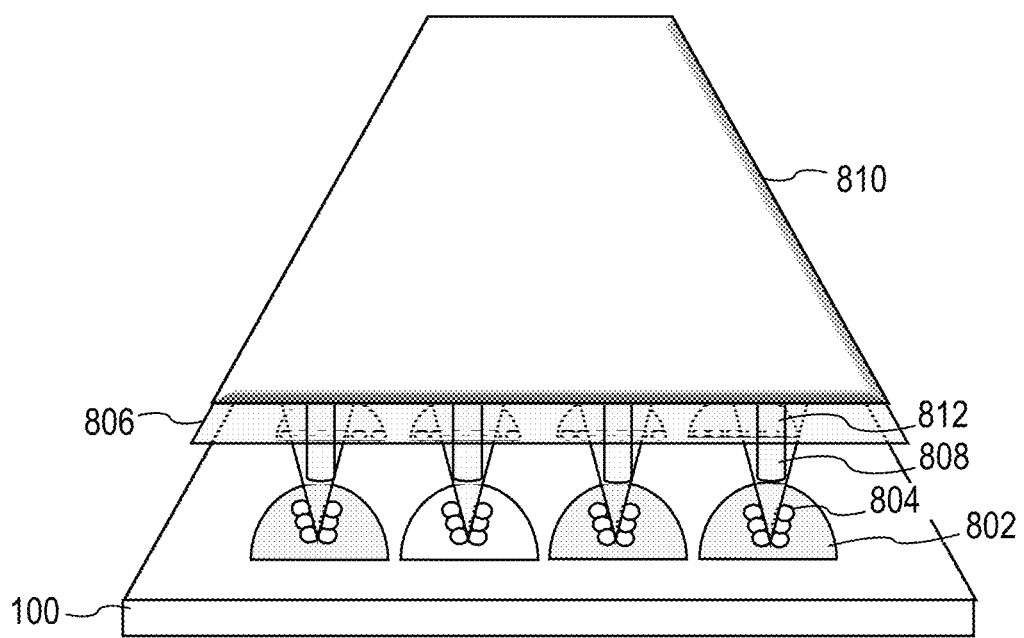

FIG. 8C illustrates that magnetic pin array 810 is moved so that magnetic pin 812 is placed within protrusion 808. Magnetic pin 812 attracts magnetic components 804 in first solution 802, and magnetic components 804 are placed on a wall of protrusion 808.

Figure 8D:
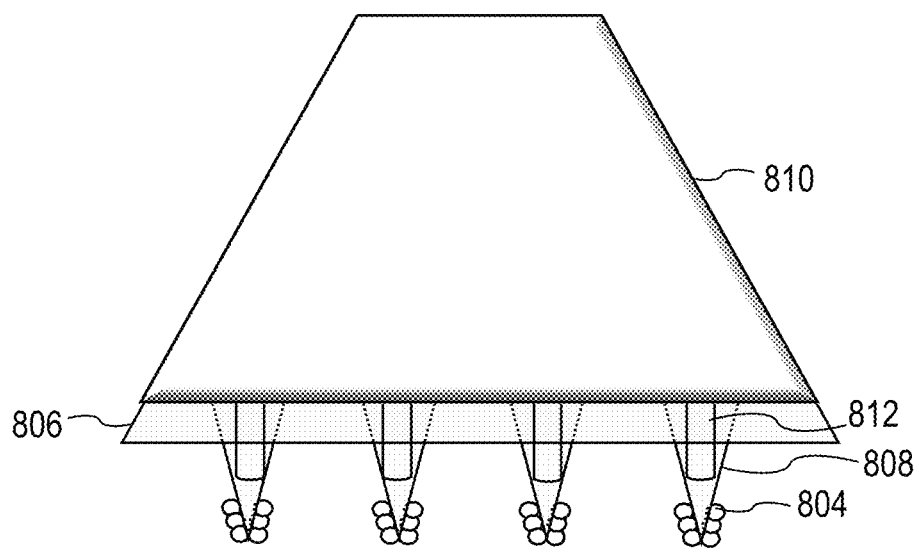

FIG. 8D illustrates that separation layer 806 and magnetic pin array 810 are separated from first solution 802 (e.g., separation layer 806 and magnetic pin array 810 are moved away from first solution 802; and/or array plate 100 is moved away from separation layer 806 and magnetic pin array 810) so that protrusion 808 is no longer in contact with first solution 802 on sample region 120. Magnetic components 804 remain on the wall of protrusion 808.

Figure 8E:
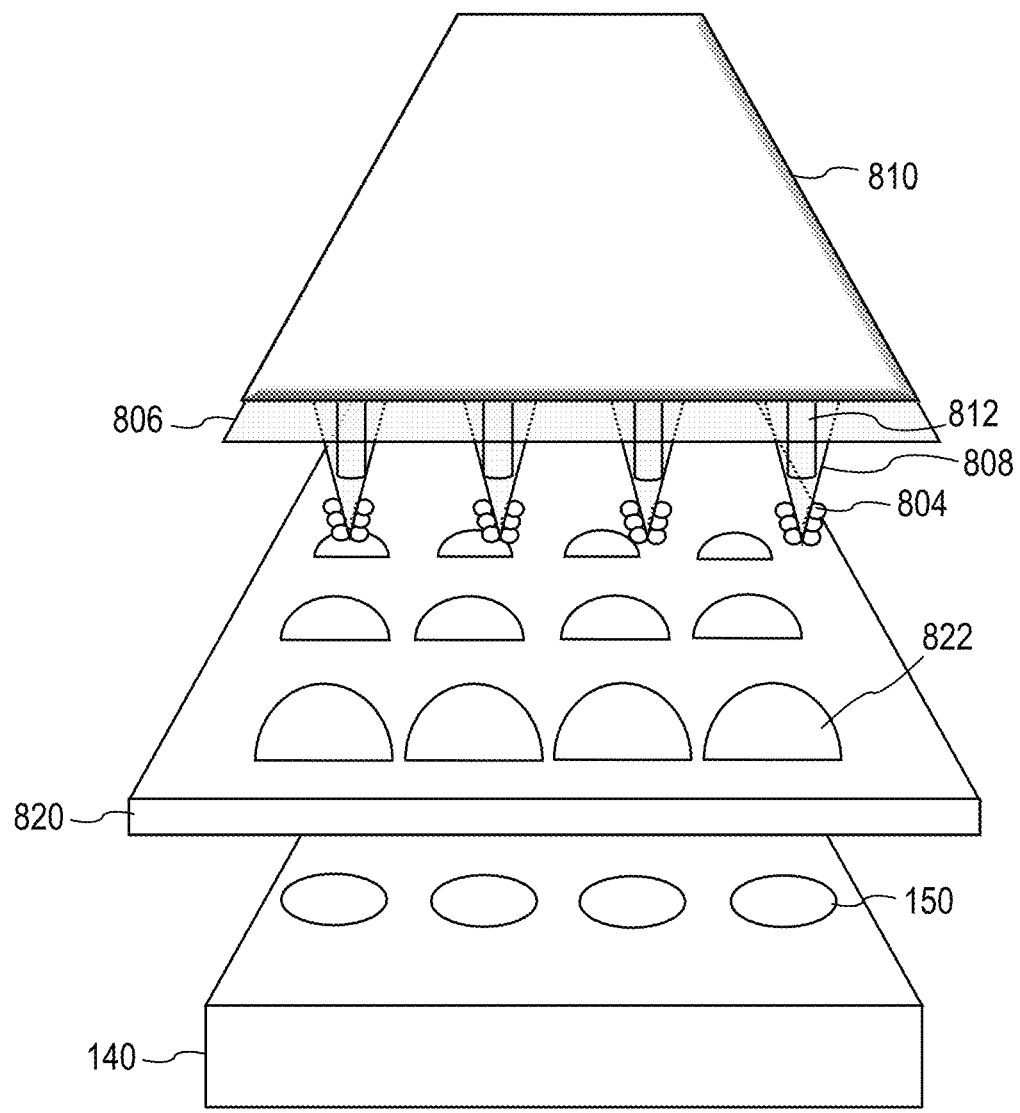

FIG. 8E illustrates that separation layer 806 and magnetic pin array 810 are positioned over second array plate 820. Second solution 822 (e.g., an elution buffer) is placed on a sample region of second array plate 820.

FIG. 8E also illustrates magnetic device plate 140 with magnetic devices 150.

Figure 8F:
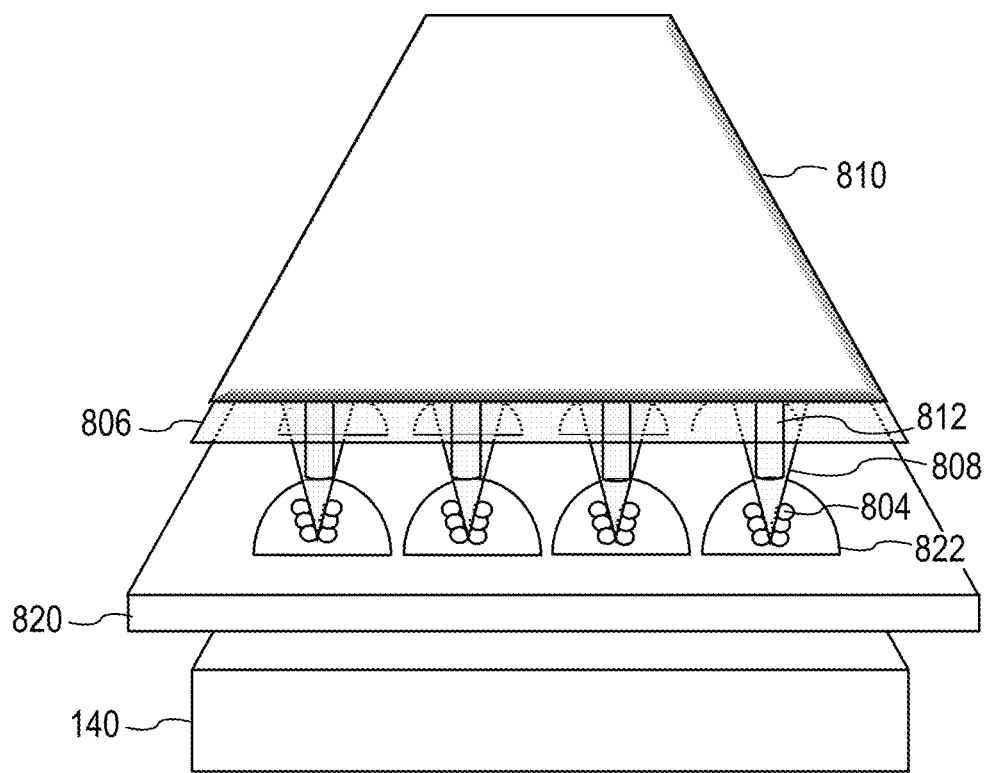

FIG. 8F illustrates that separation layer 806 and magnetic pin array 810 are placed adjacent to second array plate 820 so that magnetic components 840 on the wall of protrusion 808 are immersed in second solution 822.

FIG. 8F also illustrates that magnetic device plate 140 is placed adjacent to second array plate 820 (e.g., magnetic device plate 140 is placed underneath second array plate 820).

Figure 8G:
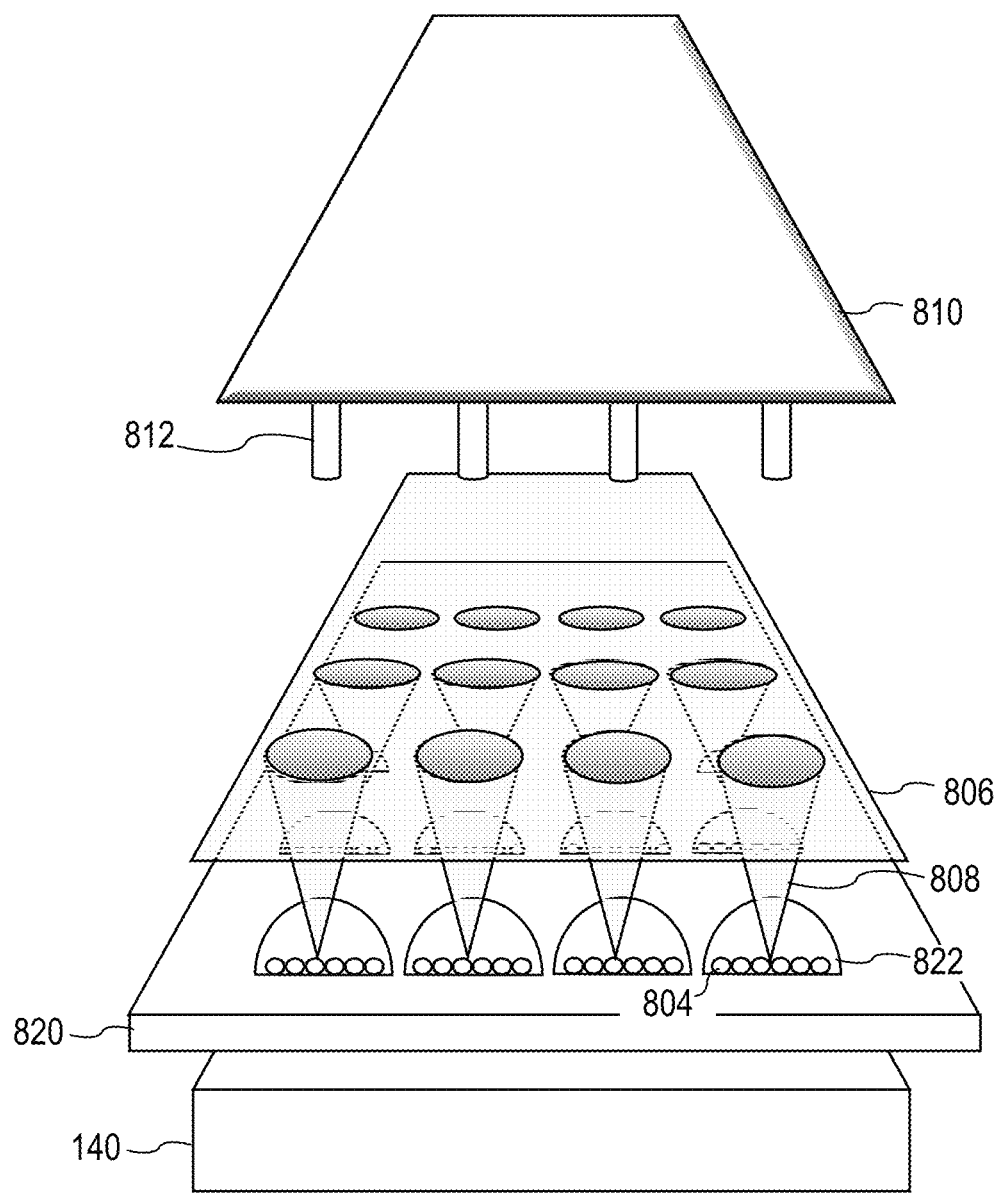

FIG. 8G illustrates that magnetic pin array 810 is separated from separation layer 806 (e.g., magnetic pin array 810 is moved away from separation layer 806 and/or separation layer 806 is moved away from magnetic pin array 810). As a result, magnetic pin 812 is also separated from protrusion 808 of separation layer 806.

FIG. 8G also illustrates that magnetic components 804 are released from protrusion 808 into second solution 822. When second solution 822 includes an elution buffer, target molecules coupled with magnetic components 804 are eluted over time (e.g., during incubation for 10 minutes).

Figure 8H:
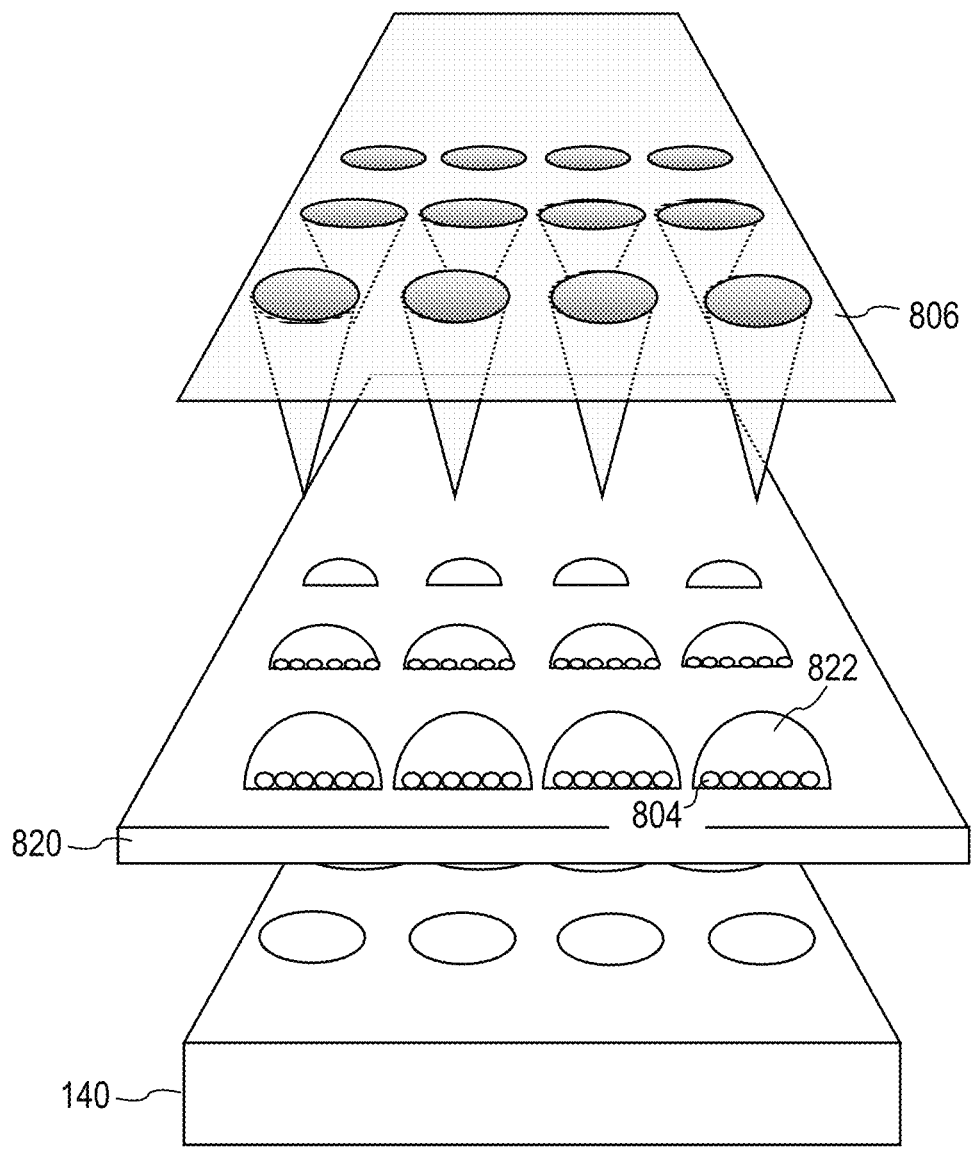

FIG. 8H illustrates that separation layer 806 is separated from second solution 822 (e.g., separation layer 806 is moved away from second solution 822, and/or second array plate 820 is moved away from separation layer 806).

FIG. 8H also illustrates that magnetic device plate 140 is separated from second array plate 820 (e.g., magnetic device plate 140 is moved away from second array plate 820 and/or second array plate 820 is moved away from magnetic device plate 140). In some embodiments, magnetic device plate 140 is separated from second array plate 820 after separation layer 806 is separated from second solution 822. In some other embodiments, magnetic device plate 140 is separated from second array plate 820 before separation layer 806 is separated from second solution 822. Alternatively, magnetic device plate 140 is separated from second array plate 820 concurrently with the separation of separation layer 806 from second solution 822.

FIGS. 8I-8L illustrate a method of retrieving supernatants from a solution containing magnetic components (e.g., magnetic beads) in accordance with some embodiments.

Figure 8I:
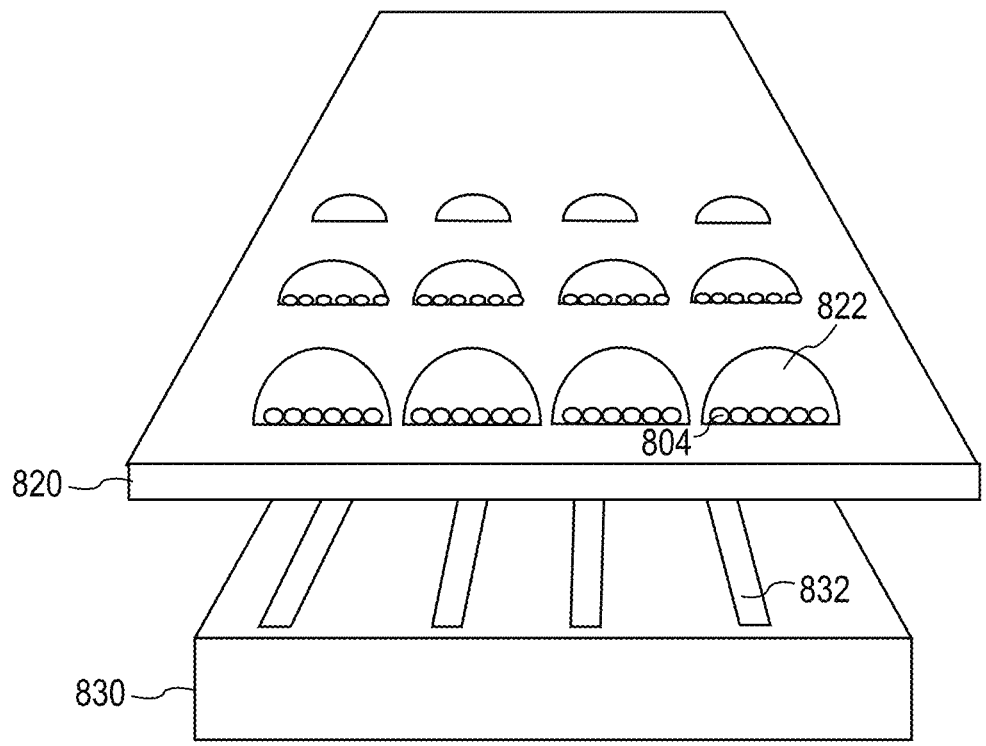
FIGS. 8I-8L illustrate a method of retrieving supernatants from a solution containing magnetic components in accordance with some embodiments.
Figure 8J:
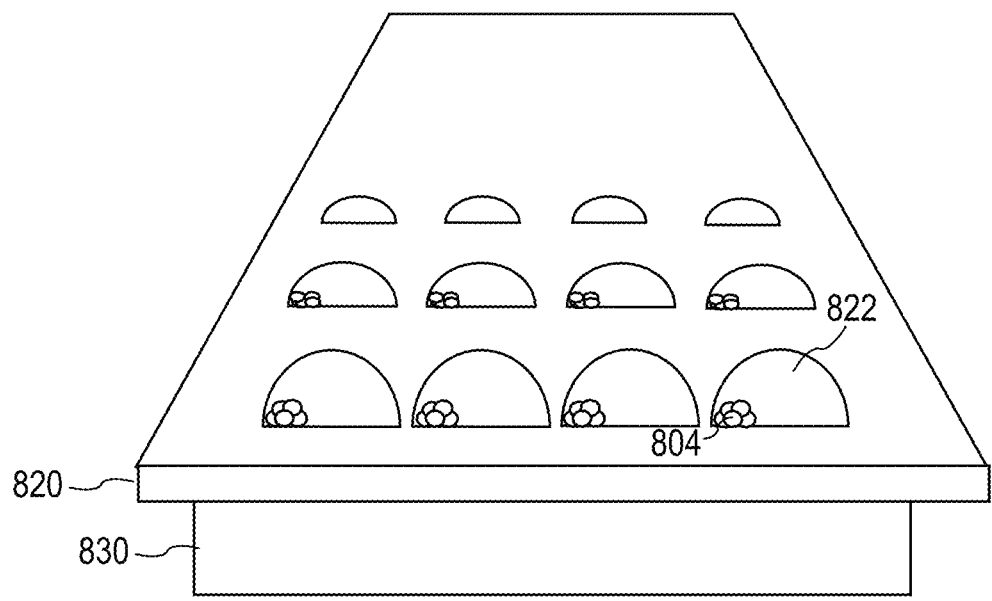

FIG. 8I illustrates magnetic device plate 830. Magnetic device plate 830 includes a plurality of linear magnetic devices 832. Linear magnetic devices 832 are positioned on magnetic device plate 320 in such a way that, when the magnetic device plate 830 is positioned adjacent to second array plate 820, magnetic devices 832 are positioned offset sample regions. As a result, when magnetic device plate 830 is positioned against second array plate 820, magnetic components 804 are aggregated and positioned offset from a center of a sample region with second solution 822, as shown in FIG. 8J.

Figure 8K:
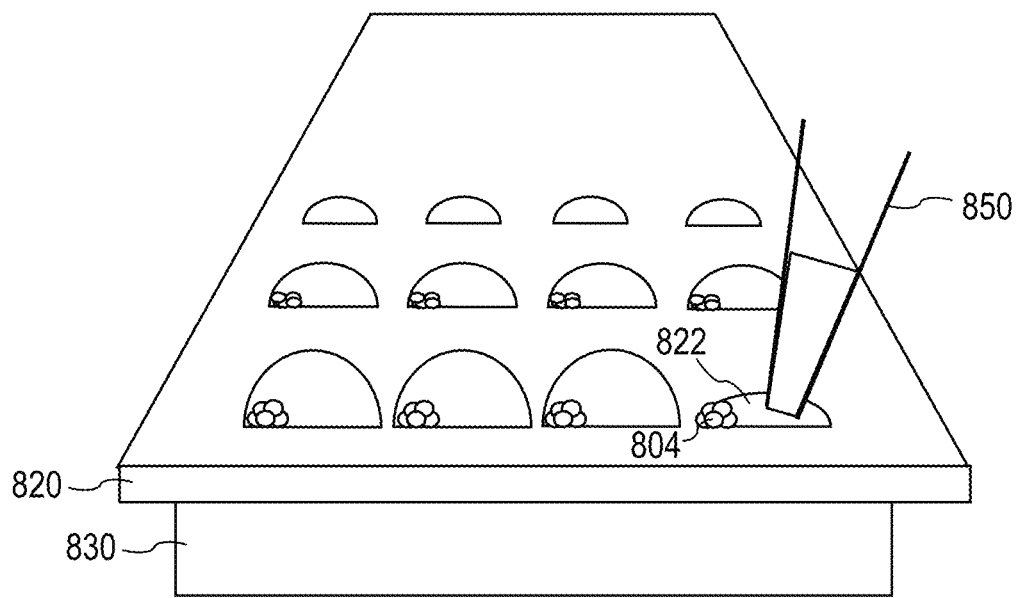

FIG. 8K illustrates that a portion of second solution 822 is aspirated (e.g., by using a pipette 850). As illustrated in FIG. 8K, a portion of second solution 822 is aspirated from a location that is away from the location of magnetic components 804. In some embodiments, the aspirated solution is analyzed. This separation of magnetic components 804 and eluted target molecules improves accuracy in determining the quantity of target molecules in second solution 822 and/or reduces malfunction of an analysis instrument configured for detecting the presence of, or analyzing the quantity of, target molecules in second solution 822.

Figure 8L:
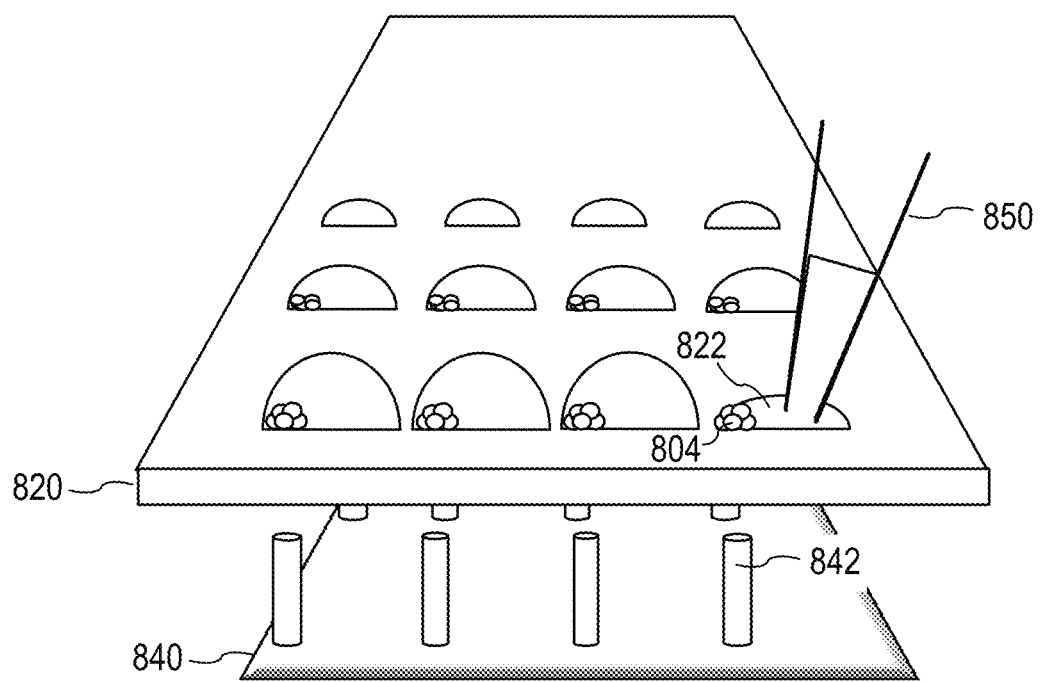

FIG. 8L illustrates that magnetic device plate 840 that includes a two-dimensional array of magnetic devices 842 is used instead of magnetic device plate 830. In FIG. 8L, magnetic devices 842 are magnetic pins (e.g., magnetic devices that have an elongated shape and are positioned substantially orthogonal to a surface of magnetic device plate 840). In some cases, magnetics with a smaller cross-section have been found to be more effective in attracting magnetic components 804.

Although the operations in FIGS. 8A-8L are described with respect to a single sample region, as illustrated in FIG. 8A-8L, analogous operations can be performed concurrently with respect to multiple sample regions on sample arrays 100 and 820. Thus, magnetic components can be retrieved from a plurality of solutions in parallel, thereby increasing the speed of retrieving the magnetic components. Similarly, magnetic components can be transferred to a plurality of solutions in parallel, thereby increasing the speed of transferring the magnetic components.

FIGS. 9A-9B are flow diagrams illustrating method 900 of retrieving magnetic components from a solution in accordance with some embodiments.

Method 900 includes (902) obtaining an array plate with a sample surface that includes a plurality of sample regions and a surrounding region (e.g., FIG. 8A). A first solution is located on a sample region of the plurality of sample regions. The first solution includes a plurality of magnetic components.

In some embodiments, the first solution includes (904) a plurality of target molecules; and respective magnetic components of the plurality of magnetic components are configured to couple with respective target molecules (e.g., FIG. 2F).

In some embodiments, the plurality of sample regions has (906) a first surface tension; and the surrounding region has a second surface tension that is distinct from the first surface tension.

Method 900 includes (908) placing a separation layer that includes one or more protrusions so that at least a respective protrusion of the one or more protrusions is at least partially immersed in the first solution (e.g., FIG. 8B).

In some embodiments, method 900 includes (910), prior to placing the separation layer: incubating the first solution; and washing the plurality of magnetic components to obtain target molecules bound to at least a subset of the plurality of magnetic components (e.g., unbound target molecules and/or detection molecules are removed, as shown in FIG. 2F).

For example, operations illustrated in FIG. 2A-2F are performed to obtain target molecules bound to at least a subset of the plurality of magnetic components. In some embodiments, detection molecules bound to the target molecules are also obtained.

In some embodiments, method 900 includes (912) incubating the first solution while one or more magnetic devices are positioned adjacent to the first solution, underneath the first solution (e.g., magnetic device plate 140 shown in FIG. 2D).

In some embodiments, method 900 includes (914) washing the plurality of magnetic components while one or more magnetic devices are positioned adjacent to the first solution, underneath the first solution (e.g., magnetic device plate 140 shown in FIG. 2F).

Method 900 includes (916) placing a first magnetic device within the respective protrusion (e.g., FIG. 8C).

Method 900 includes retrieving (918, FIG. 9B) at least a portion of the plurality of magnetic components from the first solution by separating the separation layer and the magnetic device from the first solution so that the respective protrusion ceases to be at least partially immersed in the first solution on the sample region (e.g., FIG. 8D).

In some embodiments, method 900 includes (920) obtaining a second array plate with a second sample surface that includes a second plurality of sample regions and a second surrounding region (e.g., FIG. 8E). A second solution is located on a sample region of the second plurality of sample regions. Method 900 also includes placing the separation layer and the first magnetic device adjacent to the second solution so that the retrieved portion of the plurality of magnetic components and at least a portion of the respective protrusion are immersed in the second solution (e.g., FIG. 8F); while a second magnetic device is placed adjacent to the second solution, moving the first magnetic device away from the separation layer (e.g., FIG. 8G); and, subsequent to moving the first magnetic device away from the separation layer, moving the separation layer so that the portion of the respective protrusion that was previously immersed in the second solution ceases to be immersed in the second solution (e.g., FIG. 8H).

In some embodiments, the second plurality of sample regions has a third surface tension (e.g., the second plurality of samples regions is hydrophilic) and the second surrounding region has a fourth surface tension that is distinct from the third surface tension (e.g., the second surrounding region is hydrophobic). In some embodiments, the third surface tension is identical to the first surface tension. In some embodiments, the fourth surface tension is identical to the second surface tension.

In some embodiments, method 900 includes (922) positioning the second magnetic device to move the retrieved portion of the plurality of magnetic components to a first location within the second solution (e.g., FIG. 8J); and aspirating at least a portion of the second solution from a location within the second solution that is distinct from the first location (e.g., FIG. 8K).

In some embodiments, method 900 includes (924) positioning a third magnetic device, that is distinct from the second magnetic device, to move the retrieved portion of the plurality of magnetic components to a first location within the second solution (e.g., FIG. 8L); and aspirating at least a portion of the second solution from a location within the second solution that is distinct from the first location (e.g., FIG. 8L).

In some embodiments, method 900 includes (926), prior to positioning the magnetic device, agitating the second solution. This initiates movement of the magnetic components within the second solution, which facilitates movement of the magnetic components toward the magnetic device (e.g., the second magnetic device or the third magnetic device).

In some embodiments, method 900 includes (928) analyzing the aspirated solution. For example, if the aspirated solution includes detection antibodies, labels (e.g., fluorescence molecules) on the detection antibodies are detected by a plate reader (e.g., an enzyme-linked immunosorbent assay (ELISA) plate reader).

It should be understood that the particular order in which the operations in FIG. 9 have been described is merely exemplary and is not intended to indicate that the described order is the only order in which the operations could be performed. One of ordinary skill in the art would recognize various ways to reorder the operations described herein. For example, in some cases, the first magnetic device is placed within the respective protrusion of the separation layer prior to placing the separation layer so that the respective protrusion is at least partially immersed in the first solution. Alternatively, the separation layer is placed so that the respective protrusion is at least partially immersed in the first solution, prior to placing the first magnet within the respective protrusion.

In some implementations, one or more operations described herein may be omitted. Additionally, it should be noted that details of other processes described herein with respect to other methods described herein (e.g., methods 500, 600, and 700) are also applicable in an analogous manner to method 900 described above with respect to FIG. 9. For example, the sample regions, sample solutions, magnetic components, and target molecules, described above with reference to method 900 optionally have one or more of the characteristics of the sample regions, sample solutions, magnetic components, and target molecules described herein with reference to other methods described herein (e.g., methods 500, 600, and 700). In particular, the methods for performing assays as illustrated in FIGS. 2A-2G, 3A-3D, and 4A-4K can be combined with the method for retrieving and transferring magnetic components illustrated in FIGS. 8A-8L. For brevity, many of these details are not repeated here.

It is well known to a person having ordinary skill in the art that array plates can be used in various biological and chemical reactions. Therefore, such details and specific examples are omitted for brevity.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method, comprising:
obtaining an array plate with a sample surface that includes a plurality of hydrophilic sample regions and a surrounding hydrophobic region, a respective hydrophilic sample region of the plurality of hydrophilic sample regions being surrounded by the surrounding hydrophobic region, wherein:
a sample solution is located on a hydrophilic sample region of the plurality of hydrophilic sample regions;
the sample solution includes a plurality of target molecules; and
the sample solution includes a plurality of magnetic components, respective magnetic components of the plurality of magnetic components configured to couple with respective target molecules;
while maintaining one or more magnetic devices positioned adjacent to the sample solution to retain the plurality of magnetic components on the hydrophilic sample region, incubating the sample solution so that target molecules bind to at least a subset of the plurality of magnetic components; and
washing the plurality of magnetic components to obtain the target molecules bound to at least the subset of the plurality of magnetic components.

2. The method of claim 1, including agitating the sample solution by agitating or shaking the array plate while incubating the sample solution.

3. The method of claim 1, including incubating the sample solution without agitating the sample solution.

4. The method of claim 1, including:
detecting the target molecules bound to at least the subset of the plurality of magnetic components.

5. The method of claim 4, including:
adding to the sample solution a plurality of detection molecules configured to couple with the respective target molecules; and
detecting a combination of a respective target molecule coupled with a respective magnetic component and a respective detection molecule.

6. The method of claim 5, including:
washing the plurality of magnetic components to obtain target molecules bound to at least a subset of the plurality of magnetic components and at least a subset of the plurality of detection molecules.

7. The method of claim 1, wherein the respective magnetic components have respective signatures.

8. A method, comprising:
obtaining an array plate with a sample surface that includes a plurality of hydrophilic sample regions and a surrounding hydrophobic region, a respective hydrophilic sample region of the plurality of hydrophilic sample regions being surrounded by the surrounding hydrophobic region, wherein:
a first hydrophilic sample region of the plurality of hydrophilic sample regions has a first set of magnetic components each configured to couple with a target molecule of a first type; and
a second hydrophilic sample region of the plurality of hydrophilic sample regions has a second set of magnetic components each configured to couple with a target molecule of a second type that is distinct from a target molecule of the first type;
positioning one or more magnetic devices adjacent to the first hydrophilic sample region and the second hydrophilic sample region to retain the first set of magnetic components on the first hydrophilic sample region and the second set of magnetic components on the second hydrophilic sample region;
providing a sample solution over multiple hydrophilic sample regions, including the first hydrophilic sample region and the second hydrophilic sample region, of the plurality of hydrophilic sample regions so that a single contiguous volume of the sample solution is in contact with the multiple hydrophilic sample regions, including the first hydrophilic sample region and the second hydrophilic sample region, while the first set of magnetic components on the first hydrophilic sample region and the second set of magnetic components on the second hydrophilic sample region are retained by the one or more magnetic devices;

incubating the sample solution while maintaining the one or more magnetic devices positioned adjacent to the first hydrophilic sample region and the second hydrophilic sample region to retain the first set of magnetic components on the first hydrophilic sample region and the second set of magnetic components on the second hydrophilic sample region; and washing at least one of the first set of magnetic components and the second set of magnetic components to obtain target molecules bound to at least one of at least a subset of the first set of magnetic components on the first hydrophilic sample region and at least a subset of the second set of magnetic components on the second hydrophilic sample region.

9. The method of claim 8, wherein:

the first hydrophilic sample region of the plurality of hydrophilic sample regions has a third set of magnetic components each configured to couple with a target molecule of a third type that is distinct from a target molecule of the first type and a target molecule of the second type; and the second hydrophilic sample region of the plurality of hydrophilic sample regions has a fourth set of magnetic components each configured to couple with a target molecule of a fourth type that is distinct from a target molecule of the first type, a target molecule of the second type, and a target molecule of the third type.

10. The method of claim 9, wherein:

the first set of magnetic components is associated with a first signal;

the second set of magnetic components is associated with a second signal that is distinct from the first signal;

the third set of magnetic components is associated with a third signal; and the fourth set of magnetic components is associated with a fourth signal that is distinct from the third signal.

11. The method of claim 10, wherein the third signal is identical to either the first signal or the second signal.

* * * * *